United States Patent
Feng et al.

(10) Patent No.: US 12,213,716 B1
(45) Date of Patent: Feb. 4, 2025

(54) FRAME-TYPE SURGICAL ROBOT FOR FRACTURE REDUCTION

(71) Applicant: JILIN UNIVERSITY, Changchun (CN)

(72) Inventors: Mei Feng, Changchun (CN); Yanlei Gong, Changchun (CN); Xiuquan Lu, Changchun (CN); Shuxin Dong, Changchun (CN); Jiyan Wang, Changchun (CN); Xuzeng Wu, Changchun (CN)

(73) Assignee: JILIN UNIVERSITY (CN)

( * ) Notice: Subject to any disclaimer, the term of this patent is extended or adjusted under 35 U.S.C. 154(b) by 0 days.

(21) Appl. No.: 18/820,328

(22) Filed: Aug. 30, 2024

(51) Int. Cl.
 *A61B 17/88* (2006.01)
 *A61B 34/30* (2016.01)
 *A61B 17/56* (2006.01)

(52) U.S. Cl.
 CPC .......... *A61B 17/8866* (2013.01); *A61B 34/30* (2016.02); *A61B 2017/564* (2013.01)

(58) Field of Classification Search
 CPC ......... A61B 17/88; A61B 17/56; A61B 17/62; A61B 17/17; A61B 17/1703; A61B 34/30; A61B 34/00; A61B 90/00; A61B 90/36; A61B 90/361; G06F 17/00
 See application file for complete search history.

(56) References Cited

U.S. PATENT DOCUMENTS

2023/0364557 A1   11/2023  Hoyda et al.

FOREIGN PATENT DOCUMENTS

| | | |
|---|---|---|
| CN | 104055563 A | 9/2014 |
| CN | 107753234 A | 3/2018 |
| CN | 109330686 A | 2/2019 |
| CN | 112370290 A | 2/2021 |
| CN | 115634033 A | 1/2023 |
| CN | 116942392 A | 10/2023 |
| CN | 117064556 A | 11/2023 |
| WO | 2014005457 A1 | 1/2014 |
| WO | 2015152679 A1 | 10/2015 |
| WO | 2017017443 A1 | 2/2017 |
| WO | 2023020237 A1 | 2/2023 |

*Primary Examiner* — Christopher J Beccia

(57) ABSTRACT

The present invention pertains to fracture reduction technology and introduces a frame-type surgical robot for fracture reduction. This robot comprises a mobile end mechanism and a fixed end mechanism, connected by a connection component. The mobile end mechanism includes a traction component linked to a lifting component via a translation component, which in turn is connected to a flipping component through a swing component. The flipping component features a self-rotating component, equipped with a mobile end clamping component. The fixed end mechanism includes an auxiliary traction structure, auxiliary translation structure, hand-cranking lifting structure, auxiliary flipping structure, and a fixed end clamping component. During surgery, the robot is positioned above the operating bed to perform fracture reduction. The frame-type surgical robot offers high load capacity, compact structure, small footprint, and wide motion range, combining manual and electric adjustments for easy operation and strong applicability.

8 Claims, 25 Drawing Sheets

FRAME-TYPE SURGICAL ROBOT FOR FRACTURE REDUCTION

TECHNICAL FIELD

The present invention relates to the field of fracture reduction technology, in particular to a frame-type surgical robot for fracture reduction.

BACKGROUND ART

Clinical orthopedics is mainly divided into spinal surgery, joint surgery, trauma surgery, etc., in terms of application scenarios, the development of surgical robots in the field of spinal surgery and joint surgery has been relatively mature, however, due to the difficulty of research and development of fracture reduction robots in traumatic orthopedics, its research and development progress is relatively slow, and few mature products are entering clinical applications worldwide.

At present, the conventional traumatic orthopedic fracture surgery is mainly carried out by manual reduction, that is, one or more assistants hold the fracture site by bare hand or through Kirschner wire, hand drill, and other auxiliary instruments, and then the doctor is responsible for the prying reduction of the broken bone. This operation method mainly has the following problems: ① reduction force is difficult to maintain, and sometimes multiple traction adjustments are required to complete the reduction, which is easy to cause secondary damage to the patient; ② the reduction accuracy is low, in order to achieve anatomical reduction, the patient's lesion site needs to be cut open, resulting an increase in the wound, which is not conducive to postoperative recovery; ③ the assistant doctor can only complete the auxiliary work, and the core link of the reduction still needs to be completed by the experienced surgeon, and the surgical effect is heavily dependent on experience; ④ due to the large antagonistic force of the femur, multiple assistants are often required to cooperate to complete the traction, resulting in an increase in the number of operating room personnel and an increased risk of personnel contamination. In addition, the fracture reduction auxiliary instruments used in clinical practice at this stage are mostly pure manual or semi-automatic operation modes, which require manual adjustment by doctors, the operation is complicated and the positioning is not accurate, and most of the instruments only have a single linear degree of freedom, and fracture reduction operation cannot be performed on all six-degree-of-freedom in three-dimensional space.

The application of computer and robot technology to fracture treatment surgery to develop a new generation of digital orthopedic surgery medical equipment has become an important way to solve the above problems. At present, although some domestic and foreign colleges and universities have carried out active research on orthopedic robot systems, and some products have been industrialized, such as the Mazor X navigation system launched by Medtronic, the Stryker Mako joint surgery system, and the TINAVI TiRobot orthopedic surgical system, however, the system is mainly used for preoperative planning and intra-operative navigation of orthopedic surgery and does not have the function of fracture reduction. In the field of trauma orthopedics, Beijing Rossum Robot has launched a surgical robot system with a reduction function, which is the first to realize the assisted fracture reduction technology in the world, but the system still needs more manual intervention during the operation, and the reduction force and stroke provided by it for pelvic fracture reduction are difficult to fully meet the clinical needs.

The fracture reduction robot system in the existing research is mainly divided into the series type and parallel type, which mainly have the following problems: the series type system has low positioning accuracy, low load/weight ratio, and large volume, and the robot is easy to collide with medical personnel and medical equipment during use, resulting in operational safety problems; the working space of the parallel system reset operation is limited, especially the rotation angle range around the longitudinal axis is very small, which cannot meet the actual needs, and the multi-link parallel structure is easy to block the ray, which affects the shooting effect of the X-ray film, motion control is very complicated for the complex reset operation. In addition, the individual differences of fracture patients are large, and the image processing of broken bones is difficult, most of the existing system prototypes remain in the experimental stage of laboratory model and cadaver limb operation.

SUMMARY OF THE INVENTION

In order to solve the problems in the above background technology, the present invention provides a frame-type surgical robot for fracture reduction, which not only has a high load, a compact structure, a small footprint, and a wide range of motion but also combines manual and electric adjustment, which is a simple operation and a strong applicability.

In order to achieve the above objectives, the present invention provides a frame-type surgical robot for fracture reduction, comprising a mobile end mechanism and a fixed end mechanism, the mobile end mechanism is connected to the fixed end mechanism through a connection component, and the fixed end mechanism is provided with an operating bed for a patient to lie flat, the mobile end mechanism comprises a traction component, the traction component is connected to a lifting component through a translation component, the lifting component is connected to a flipping component through a swing component, the flipping component is provided with a self-rotating component, and the self-rotating component is provided with a mobile end clamping component; the fixed end mechanism comprises an auxiliary traction structure, the auxiliary traction structure is connected to a hand-cranking lifting structure through an auxiliary translation structure, the hand-cranking lifting structure is connected to an auxiliary flipping structure through a flipping fixed structure, the auxiliary flipping structure is provided with a fixed end clamping component, during the operation, a surgical robot is placed above the operating bed to complete the fracture reduction operation of the patient.

Preferably, the traction component comprises a support frame, the side and top end of the support frame are provided with a support frame sheet metal, the bottom end of the support frame is connected to a caster through a hole flat connector, the support frame is provided with a motor support plate, the motor support plate is provided with a traction push rod, the two sides of the traction push rod are provided with a traction guide rail, the traction guide rail is arranged on the support frame, the traction push rod is connected to a push rod mounting frame through a push rod bracket, the push rod mounting frame is fixed on the support frame, and the support frame sheet metal at the top is provided with a traction organ cover for protection; the support frame is provided with a cross-bed connecting rod and a counterweight block, the counterweight block is provided with a storage box, the storage box is connected to the counterweight block through a bulge.

Preferably, the translation component comprises a translation bottom plate, the bottom of the translation bottom plate is provided with a module connector, a movable rod of the traction push rod is connected to the module connector, the bottom of the translation bottom plate is provided with a traction slider, and the traction slider is slidably connected to the traction guide rail; the top of the translation bottom plate is covered with a translation sheet metal, and the translation sheet metal is provided with a translation organ cover for protection, the two ends of the translation bottom plate are respectively provided with a translation side plate and a translation motor plate, a translation screw is arranged between the translation side plate and the translation motor plate, both sides of the translation screw is provided with a translation guide rail, the translation guide rail is arranged on the translation bottom plate, the two ends of the translation screw are respectively connected to the translation side plate and the translation motor plate through a translation bearing, the translation motor plate is provided with a translation motor, the output shaft of the translation motor is in transmission connection with one end of the translation screw through a translation synchronous belt component, one side of the translation motor plate is fixed with a tensioning bulge for the tensioning of the translation synchronous belt component, the tensioning bulge is connected to a translation tensioning plate through a single bolt, and the translation bottom plate is provided with a translation limit part for translation limit.

Preferably, the lifting component comprises a lifting bottom plate, the lifting bottom plate is connected to a translation slide through a slide side plate, the bottom end of the translation slide is provided with a connecting seat and a translation slider, the translation slider is slidably connected to the translation guide rail, the translation slider is arranged on both sides of the connecting seat, the connecting seat is provided with a screw nut, the screw nut is sleeved on the translation screw and rotationally connected to the translation screw, and the translation slide is provided with a translation baffle for the translation limit; the upper of the lifting bottom plate is covered with a lifting sheet metal, the lifting sheet metal is provided with a lifting organ cover for protection, both ends of the lifting bottom plate is provided with a lifting side plate and a lifting motor plate, a lifting screw is arranged between the lifting side plate and the lifting motor plate, both sides of the lifting screw is provided with a lifting guide rail, the lifting guide rail is arranged on the lifting bottom plate, the two ends of the lifting screw are respectively connected to the lifting side plate and the lifting motor plate through a lifting bearing, the lifting motor plate is provided with a lifting motor, the output shaft of the lifting motor is in transmission connection with one end of the lifting screw through a lifting synchronous belt component, one side of the lifting motor plate is fixed with a lifting bulge for the tensioning of the lifting synchronous belt component, the lifting bulge is connected to a lifting tensioning plate through a single bolt, and the lifting bottom plate is provided with a lifting limit part for lifting limit.

Preferably, the swing component comprises a sensor fixed plate, the sensor fixed plate is connected to a lifting seat through a lifting slide, the lifting seat is provided with a lifting nut, the lifting nut is sleeved on the lifting screw and is rotatably connected to the lifting screw, the two sides of the lifting seat are provided with a lifting slider, one side of the lifting slider is connected to a lifting slide, the other side of the lifting slider is slidably connected to the lifting guide rail, and the lifting slide is provided with a lifting baffle for the lifting limit; the sensor fixed plate is provided with a sensor, and the sensor is connected to a sensor adapter plate, the sensor adapter plate is provided with a swing reducer, and the swing reducer is connected to the output shaft of a swing motor, the lifting slide is connected to a swing sheet metal, and the swing sheet metal is covered on the sensor fixed plate, sensor, sensor adapter plate, swing reducer and swing motor.

Preferably, the flipping component comprises a support frame, the support frame is provided with an array hole, and the swing reducer is connected to the support frame through an array hole; one end of the support frame is provided with a left lug with a left groove and an installation groove, the other end of the support frame is provided with a right lug with a right groove, the left groove and the right groove are respectively provided with a flipping bearing, the left lug is provided with a flipping limit part for limiting the flipping limit, the support frame is provided with a step surface, the step surface is provided with a flipping reducer, the flipping reducer is connected to the output shaft of a flipping motor, the flipping reducer is in transmission connection with a flipping synchronous belt component, a flipping motor plate is arranged between the flipping reducer and the flipping synchronous belt component, the flipping motor plate is provided with a straight groove for adjusting the tension of the flipping synchronous belt component, the straight groove is provided with an installation hole, the installation hole is arranged on the support frame, and the upper of the support frame is covered with a flipping sheet metal.

Preferably, the self-rotating component comprises a gearbox, the two ends of the gearbox are respectively provides with a left shaft and a right shaft, the gearbox is connected to the flipping bearing of the left groove of the support frame through the left shaft, the left shaft is provided with a left shaft snap ring and a flipping baffle for the flipping limit, the gearbox is connected to the flipping bearing of the right groove of the support frame through the right shaft, the right shaft is provided with a right shaft snap ring, and the right shaft passes through the right groove of the support frame and is rotationally connected to the flipping synchronous belt component; the gearbox is provided with a front cover plate, the gearbox is provided with a gear, the outer surface of the gearbox is provided with a joint motor, the output shaft of the joint motor is connected to the gear, the gear is meshed with a ring gear, and the ring gear is slidably connected to the gearbox through a roller, a rear insert strip is arranged between one side of the ring gear and the gearbox, a front insert strip is arranged between the other side of the ring gear and the front cover plate, and the ring gear is provided with linear bearings; the gearbox is provided with a clamping seat, and the clamping seat is provided with a locking handle.

Preferably, the mobile end clamping component comprises four optical shafts, four optical shafts are connected to the ring gear through the linear bearing, and the optical shaft is clamped in the clamping seat; one end of the four optical shafts is provided with a carbon ring, the other end of the two optical shafts is connected to a left inner splint, the other end of the other two optical shafts is connected to a right inner splint, one end of the left inner splint is connected to a left outer splint through a rotating shaft, the other end of the left inner splint is connected to the left outer splint through a rotating handle, one end of the right inner splint is connected to a right outer splint through the rotating shaft, the other end of the right inner splint is connected to the right outer splint through the rotating handle, a Kirschner wire is clamped between the left inner splint and the left outer splint, and between the right inner splint and the right outer splint.

Preferably, the auxiliary traction structure comprises a fixed frame, both sides and the top of the fixed frame are provided with a shell, the bottom of the fixed frame is connected to an auxiliary caster through a connecting plate, the top of the fixed frame is provided with a fixed plate, the fixed plate is provided with a guide rail I, the guide rail I is arranged in the shell at the top of the fixed frame, and the shell at the top of the fixed frame is provided with an organ cover I for protection;

- the auxiliary translation structure comprises a bottom plate I, the bottom end of the bottom plate I is provided with a slider I, and the slider I is slidably connected to the guide rail I, the bottom end of the bottom plate I is connected to a traction gripper through a cushion block I, the upper of a connecting bottom plate I is covered with a rectangular shell, and the rectangular shell is provided with an organ cover II, the top of the bottom plate I is provided with a guide rail II;
- the hand-cranking lifting structure comprises a bottom plate II, one side of the bottom plate II is provided with an L-shaped plate, the bottom end of the L-shaped plate is provided with a slider II, the slider II is slidably connected to the guide rail II, the bottom end of the L-shaped plate is connected to a translation gripper through a cushion block II, both ends of the bottom plate II are provided with a vertical plate, the other side of the bottom plate II is provided with a guide rail III and a screw I, both ends of the screw I are connected to the vertical plate through an auxiliary bearing, one end of the screw I is provided with a handwheel, the bottom plate II is connected to an L-shaped shell, the L-shaped shell is covered on the screw I, the guide rail III and the L-shaped plate, and the L-shaped shell is provided with an organ cover III;
- the flipping fixed structure comprises a square plate, the square plate is provided with a padding plate, the padding plate is provided with a slider III, the slider III is slidably connected to the guide rail III, the square plate is provided with a moving seat, and the moving seat is rotationally sleeved on the screw I;
- the auxiliary flipping structure comprises an upper U-shaped ear plate, the upper U-shaped ear plate connected to the square plate, the upper U-shaped ear plate connected to a lower U-shaped ear plate through a pressing shaft, the pressing shaft is provided with an eccentric wheel, the eccentric wheel is provided with a handle, the bottom end of the lower U-shaped ear plate is provided with an arc plate, an auxiliary linear bearing is arranged in the arc plate, the side of the arc plate is provided with an auxiliary clamping seat, and the auxiliary clamping seat is provided with an auxiliary handle;
- the fixed end clamping component and the mobile end clamping component adopt the same structure, the optical shaft of the fixed end clamping component is connected to the arc plate through the auxiliary linear bearing, and the optical shaft of the fixed end clamping component is clamped in the auxiliary clamping seat.

Preferably, the connection component comprises two single-ended bent rods, one end of the single-ended bent rod is connected to the support frame through a bent rod base plate, and the other end of the single-ended bent rod is rotationally connected to one end of a slotted bent rod through the rotating shaft, the other end of the slotted bent rod is rotationally connected to one end of a trimming bent rod through the rotating shaft, the other end of the trimming bent rod is rotationally connected to one end of the other single-ended bent rod through the rotating shaft, and the other end of the single-ended bent rod is connected to the fixed frame through the bent rod base plate, a locking sleeve is slidably arranged on the single-ended bent rod, slotted bent rod and trimming bent rod.

Therefore, the present invention adopts a frame-type surgical robot for fracture reduction with the above structure, which has the following beneficial effects:

(1) a surgical robot for fracture reduction of the present invention adopts a hybrid structure, which is used to realize the six-degree-of-freedom joint series of the mobile end mechanism for the reduction operation action, the fixed end mechanism for fixing the proximal end of the fracture also adopts a series structure, the end of mobile and fixed respectively realize the motion of the distal end of the fracture and the fixation of the proximal end of the fracture, and the two components are connected together through the connecting rod to form a whole with high load, which can meet the difference of the reduction force of individual patients;

(2) both ends of the frame-type surgical robot for fracture reduction of the present invention are cantilever structures, so that there is enough space on the side, and the space is larger than the width of a human body, which can provide sufficient operating space for the doctor to deal with intra-operative emergencies and ensure the safety of robot surgery;

(3) the frame-type surgical robot for fracture reduction of the present invention adopts a frame-type structure, which is arranged along the bed during use, it has the characteristics of a compact structure, saves the operating room space, avoids the problem of equipment collision, and has a wide range of six-degree-of-freedom motion, which is suitable for different reduction requirements;

(4) the frame-type surgical robot for fracture reduction of the present invention can be folded and retracted, the expansion and contraction of the mobile end mechanism and the fixed end mechanism can be realized by a contraction connection component, and the occupied area is small;

(5) the end clamping part of the frame-type surgical robot for fracture reduction of the present invention adopts a carbon fiber structure, which does not block the X-ray, can improve the image shooting quality, and is convenient for the doctor to read the X-ray film information (6) the frame-type surgical robot for fracture reduction of the present invention has a large range of motion along the width of the bed, when the left leg or right leg of different patients needs to be operated, or the affected limb needs to be replaced during the operation, the robot does not need to be rearranged, and the above action can be realized only by moving the translation component, and the operation is simple;

(7) the frame-type surgical robot for fracture reduction of the present invention is combined with manual and electric adjustment, each joint of the mobile end adopts an active form and can be controlled by a host computer, the fixed end and the clamping components are manually adjusted, the operation is simple and can realize the robot connection operation of different surgical requirements;

(8) the frame-type surgical robot for fracture reduction of the present invention is provided with a locking structure and a limit structure, the active joint is provided with a limiter, the passive joint is provided with a locking structure such as a gripper and a hand-cranking screw, and the safety is high;

(9) the frame-type surgical robot for fracture reduction of the present invention integrates a six-dimensional force torque sensor, which can detect the change of force during the reduction process, so as to ensure that the reduction action does not exceed the human body's acceptance limit and ensure patient safety;

(10) the end clamping component of the frame-type surgical robot for fracture reduction of the present invention can adjust the relative position and posture, which can meet the clamping requirements of different positions and postures of the Kirschner wire entered by the doctor each time, and has stronger applicability.

Further detailed descriptions of the technical scheme of the present invention can be found in the accompanying drawings and embodiments.

DRAWING MARKS

Figure 1:
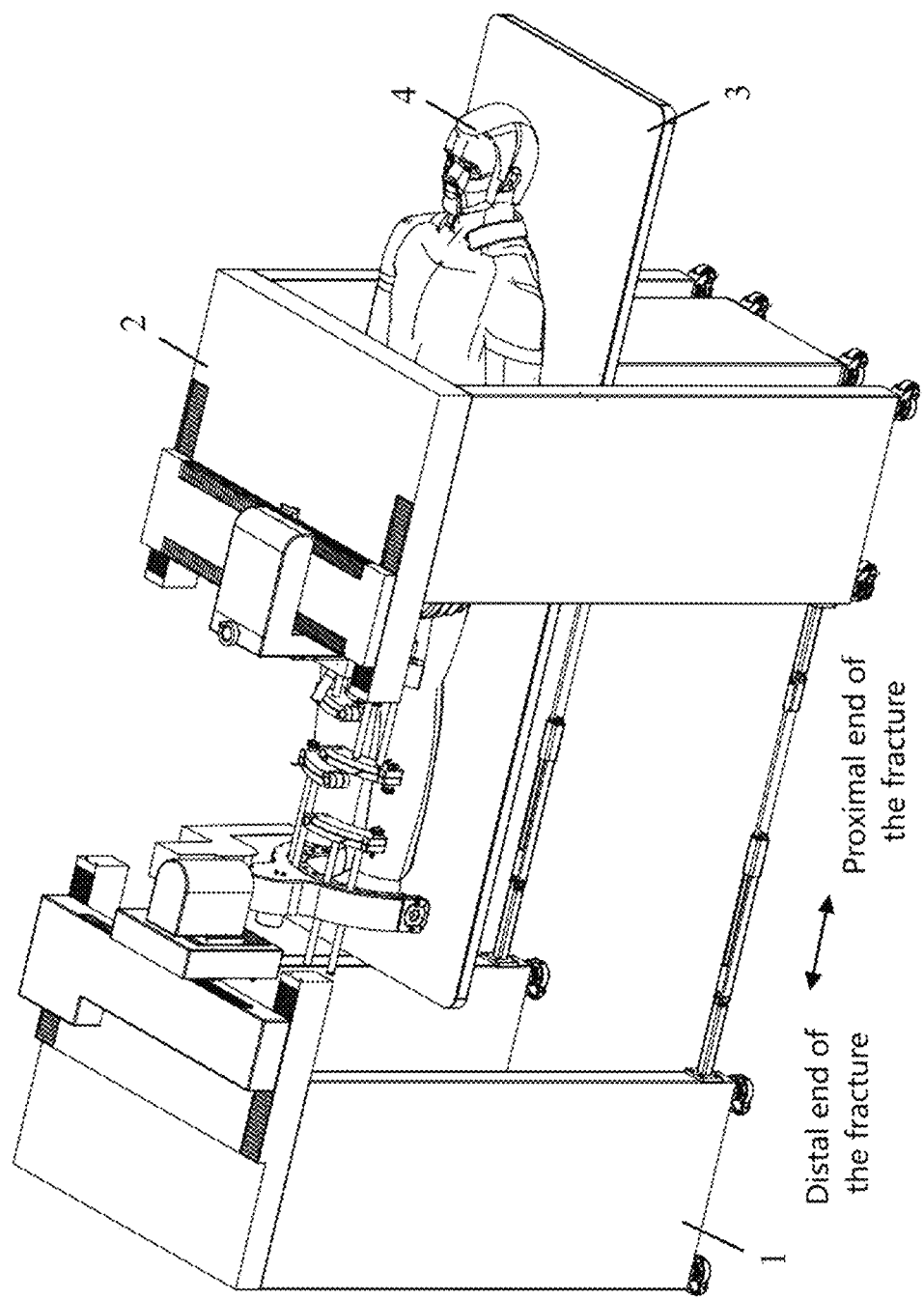
FIG. 1 is a schematic diagram of an overall structure of a frame-type surgical robot for fracture reduction according to an embodiment of the present invention.

1, a mobile end mechanism; 2, a fixed end mechanism; 3, an operating bed; 4, a patient; 11, a traction component; 12, a translation component; 13, a lifting component; 14, a swing component; 15, a flipping component; 16, a self-rotating component; 17, a mobile end clamping component; 18, a connection component; 21, an auxiliary traction structure; 22, an auxiliary translation structure; 23, a hand-cranking lifting structure; 24, a flipping fixed structure; 25, an auxiliary flipping structure; 26, a fixed end clamping component; 1101, a support frame; 1102, a support frame sheet metal; 1103, a cross-bed connecting rod; 1104, a guide rail mounting plate; 1105, a traction guide rail; 1106, a traction push rod; 1107, a push rod bracket; 1108, a push rod mounting frame; 1109, a motor support plate; 1110, a storage box; 1111, a counterweight block; 1112, a traction organ cover; 1113, a caster; 1114, a hole flat connector; 11101, a bulge; 11111, a storage groove 11111; 1201, a translation sheet metal; 1202, a translation organ cover; 1203, a translation side plate; 1204, a translation bearing; 1205, a translation guide rail; 1206, a translation bottom plate; 1207, a traction slider; 1208, a module connector; 1209, a translation motor; 1210, a translation limit part; 1211, a translation screw; 1212, a translation motor plate; 1213, a tensioning bulge; 1214, a translation tensioning plate; 1215, a translation synchronous belt component; 12011, a translation groove; 12061, a guide rail groove; 12062, a relief groove; 11061, a movable rod; 1301, a translation baffle; 1302, a translation slide; 1303, a translation slider; 1304, a connecting seat; 1305, a screw nut; 1306, a slide side plate; 1307, a lifting limit part; 1308, a lifting bottom plate; 1309, a lifting guide rail; 1310, a lifting side plate; 1311, a lifting bearing; 1312, a lifting screw; 1313, a lifting sheet metal; 1314, a lifting organ cover; 1315, a lifting motor; 1316, a lifting motor plate; 1317, a lifting bulge; 1318, a lifting tensioning plate; 1319, a lifting synchronous belt component; 13131, a lifting groove; 1401, a lifting baffle; 1402, a lifting slide; 1403, a lifting seat; 1404, a lifting slider; 1405, a lifting nut; 1406, a sensor fixed plate; 1407, a sensor; 1408, a sensor adapter plate; 1409, a swing reducer; 1410, a swing motor; 1411, a swing sheet metal; 1501, a support frame; 1502, a flipping bearing; 1503, a flipping limit part; 1504, a rubber pad; 1505, a flipping motor; 1506, a flipping reducer; 1507, a flipping motor plate; 1508, a flipping synchronous belt component; 1509, a flipping sheet metal; 15011, an installation groove; 15012, a left groove; 15013, a left lug; 15014, a right groove; 15015, a right lug; 15016, an array of holes; 15017, a step surface; 15018, an installation hole; 15071, a straight groove; 1601, a gearbox; 1602, a gear; 1603, a ring gear; 1604, a gear shaft; 1605, an oil-free bearing; 1606, a linear bearing; 1607, a front cover plate; 1608, a front insert strip; 1609, a rear insert strip; 1610, a roller bearing; 1611, a roller; 1612, a left shaft; 1613, a flipping baffle; 1614, a left shaft snap ring; 1615, a right shaft; 1616, a right shaft snap ring; 1617, a self-rotating limit part; 1618, a joint motor; 1619, a clamping seat; 1620, a locking handle; 1621, a limit screw; 16011, a motor installation hole; 16012, a rear groove; 16013, a limit groove; 16014, an arc straight groove; 16015, a shaft hole; 16016, a small bearing hole; 16017, a groove structure; 16021, a center hole; 16031, a bearing hole; 16071, a front groove; 1701, a left inner splint; 1702, a left outer splint; 1703, a right inner splint; 1704, a right outer splint; 1705, a rotating shaft; 1706, a shaft ring; 1707, a carbon ring; 1708, a plug; 1709, a rotating handle; 1710, a butterfly nut; 1711, an optical shaft; 1801, a bent rod base plate; 1802, a single-ended bent rod; 1803, a rotating shaft; 1804, a slotted bent rod; 1805, a locking sleeve; 1806, a trimming bent rod; 1807, a clip spring; 2101, a fixed frame; 2102, a shell; 2103, a fixed plate; 2104, a guide rail I; 2105, an organ cover I; 2016, a connecting plate; 2107, an auxiliary caster; 21021, a rectangular groove; 2201, a rectangular shell; 2202, a guide rail II; 2203, a bottom plate I; 2204, a slider I; 2205, a traction gripper; 2206, an organ cover II; 2207, a cushion block I; 22011, a long groove; 2301, an L-shaped shell; 2302, an organ cover III; 2303, a handwheel; 2304, a vertical plate; 2305, a screw I; 2306, an auxiliary bearing; 2307, a guide rail III; 2308, a bottom plate II; 2309, a slider II; 2310, an L-shaped plate; 2311, a translation gripper; 2312, a cushion block II; 23011, a short groove; 23012, a circular hole; 23101, a short side; 23102, a long side inner side; 2401, a square plate; 2402, a padding plate; 2403, a slider III; 2404, a moving seat; 2501, an upper U-shaped ear plate; 2502, a pressing shaft; 2503, a shaft end screw; 2504, a lower U-shaped ear plate; 2505, an eccentric wheel; 2506, a handle; 2507, an arc plate; 2508, an auxiliary linear bearing; 2509, a shaft sleeve; 2510, an auxiliary handle; 2511, an auxiliary clamping seat.

DETAILED DESCRIPTION

The technical scheme of the present invention is further explained below by drawings and embodiments.

Unless otherwise defined, the technical or scientific terms used in the invention shall be those to which the invention belongs. As used herein, the terms "first", "second", and the like do not denote any order, quantity, or importance, but rather are used to distinguish one element from another. Similar words such as "comprise" or "include" means that the elements or items preceding the word encompass the elements or items listed after the word and equivalents thereof, but do not exclude other elements or items. The terms "arranged", "mounted" and "connected" are to be understood in a broad sense, e.g. as a fixed connection, as a detachable connection, or as an integral connection; maybe a mechanical connection or an electrical connection; it can be directly connected or indirectly connected through an intermediate medium, and can be the internal connection of two components. "Up", "down", "left", "right", etc. are only used to indicate a relative positional relationship, which may change accordingly when the absolute position of the object being described changes.

Embodiment

Figure 2:
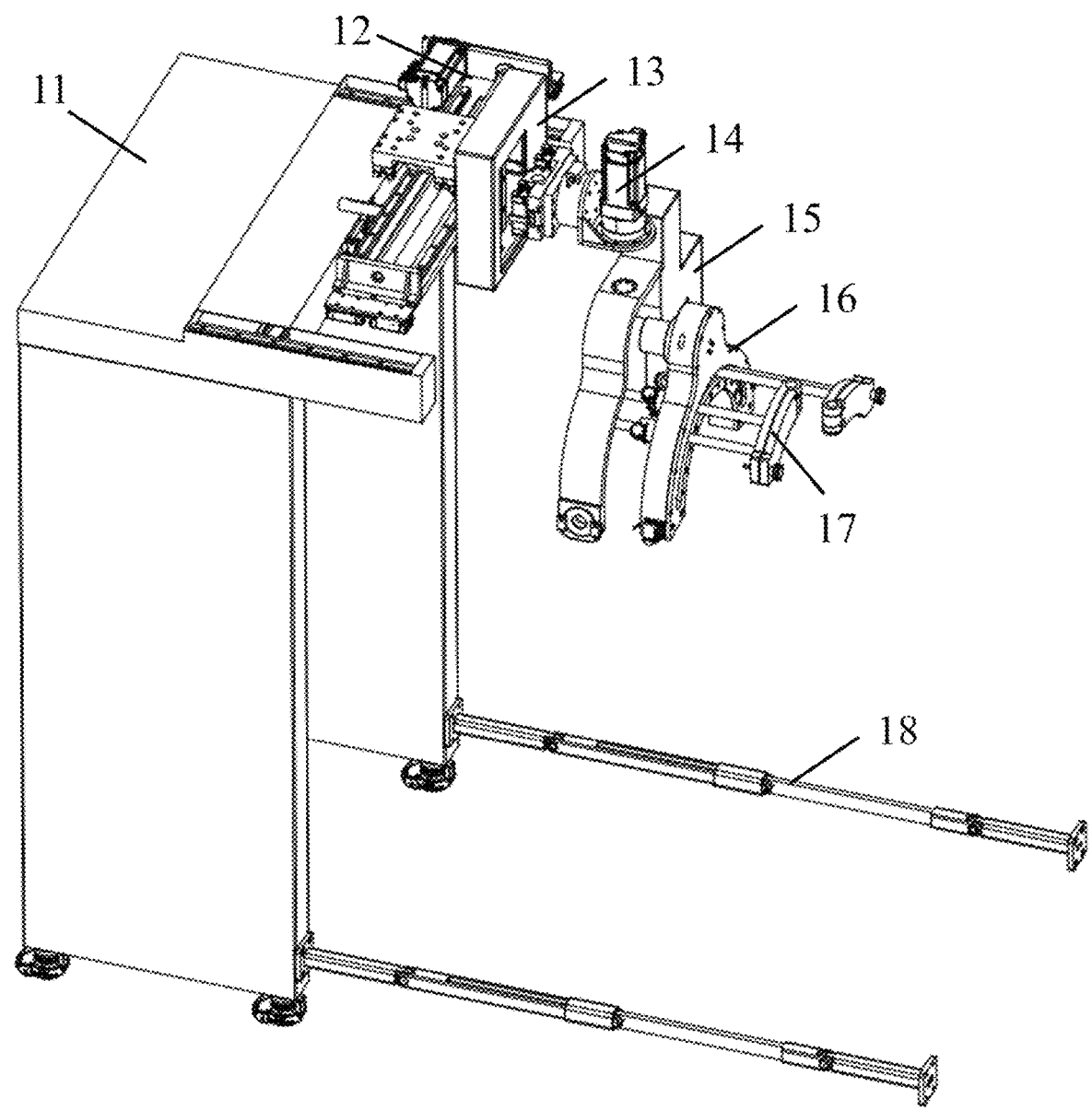
FIG. 2 is a schematic diagram of a structure of a moving mobile mechanism according to an embodiment of the present invention.
Figure 3:
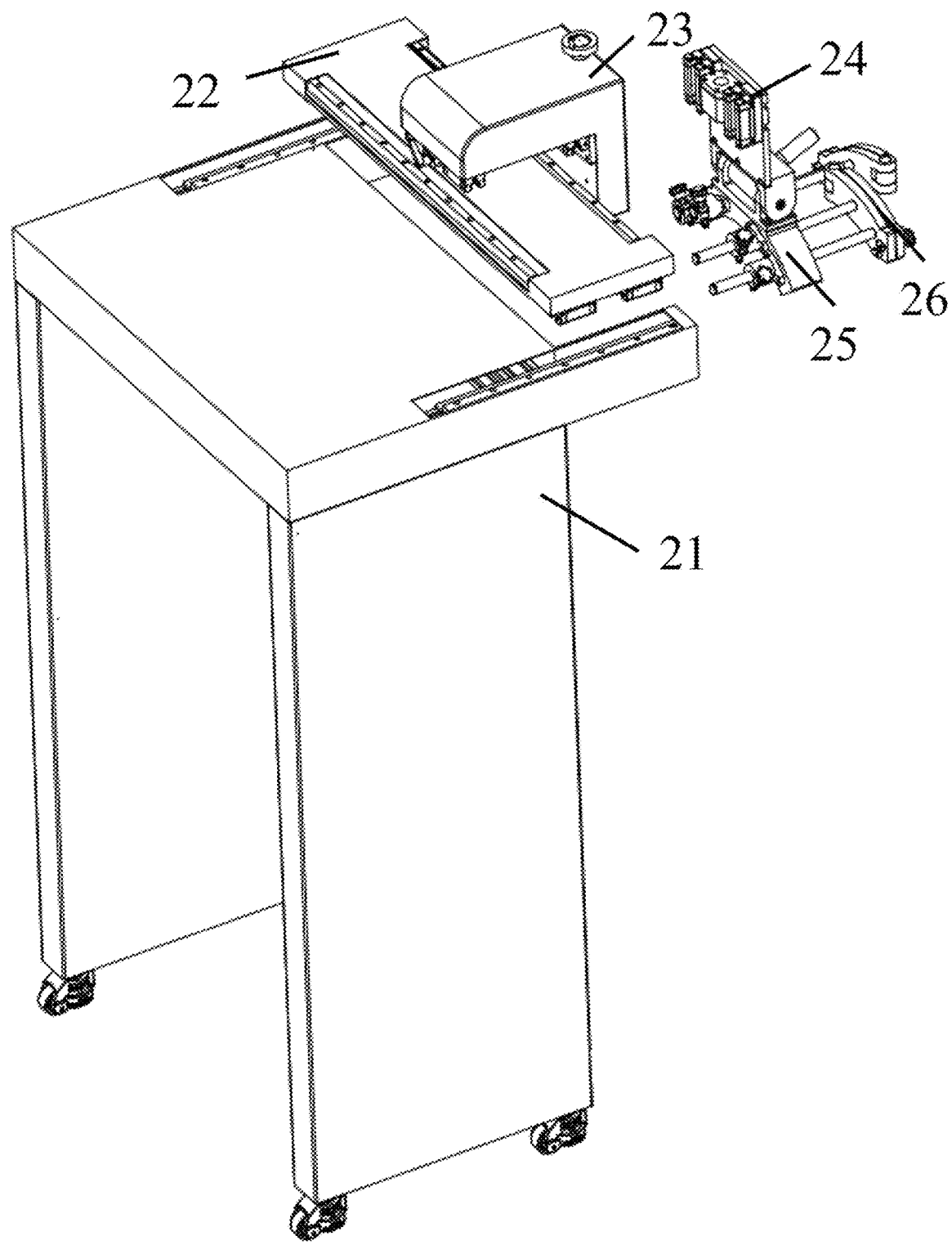
FIG. 3 is a schematic diagram of a structure of a fixed end mechanism according to an embodiment of the present invention.

As shown in FIG. 1, a frame-type surgical robot for fracture reduction of the present invention, comprising a mobile end mechanism 1 and a fixed end mechanism 2, the mobile end mechanism 1 is connected to the fixed end mechanism 2 through a connection component 18. As shown in FIG. 2, the mobile end mechanism 1 comprises a traction component 11, a translation component 12, a lifting component 13, a swing component 14, a flipping component 15, a self-rotating component 16, a mobile end clamping component 17, and a connection component 18. The traction component 11 is connected to the lifting component 13 through the translation component 12, the lifting component 13 is connected to the flipping component 15 through the swing component 14, the flipping component 15 is provided with the self-rotating component 16, and the self-rotating component 16 is provided with the mobile end clamping component 17. The spatial six-degree-of-freedom motion required for the operation of distal fracture reduction can be realized through the mobile end mechanism 1. As shown in FIG. 3, the fixed end mechanism 2 comprises an auxiliary traction structure 21, an auxiliary translation structure 22, a hand-cranking lifting structure 23, a flipping fixed structure 24, an auxiliary flipping structure 25, and a fixed end clamping component 26. The auxiliary traction structure 21 is connected to the hand-cranking lifting structure 23 through the auxiliary translation structure 22, the hand-cranking lifting structure 23 is connected to the auxiliary flipping structure 25 through the flipping fixed structure 24, the auxiliary flipping structure 25 is provided with the fixed end clamping component 26. The fixed end mechanism 2 can assist the mobile end mechanism 1 to realize the fixation of the proximal limb of the fracture, and the motion is realized by manual operation. During the operation, the surgical robot is placed above the operating bed 3 to complete the fracture reduction operation of a patient 4.

The motor output force of the mobile end mechanism 1 can ensure that the muscle antagonism force can be overcome, the fixed end mechanism 2 can ensure that the human body is fixed firmly, prevent the patient 4 body displacement caused by dragging during the reduction process, so as to ensure the surgical effect and safety of the robot operation, the mobile end mechanism 1 and the fixed end mechanism 2 are connected by the connection component 18 to form a hybrid structure as a whole, which ensures its high load and high stability. During the operation, the robot is moved to the appropriate position along the length direction of the operating bed 3, by adjusting the connection component 18 to the maximum length, the relative position of the mobile end mechanism 1 and the fixed end mechanism 2 can be fixed; after adjustment, the robot is distributed along the length direction of the bed, and the overall structure is compact, which avoids collision and interference with other equipment in the operating room, and there is sufficient standing space on both sides along the width direction of the bed, which is convenient for doctors to interfere with the operation of the robot in the case of emergency treatment, thereby improves the safety of the robot operation. At the end of the operation, by adjusting the connection component 18 again, the distance between the mobile end mechanism 1 and the fixed end mechanism 2 can be reduced, so as to reduce the overall size of the robot, reduce the occupied area, and facilitate storage and placement.

Figure 4:
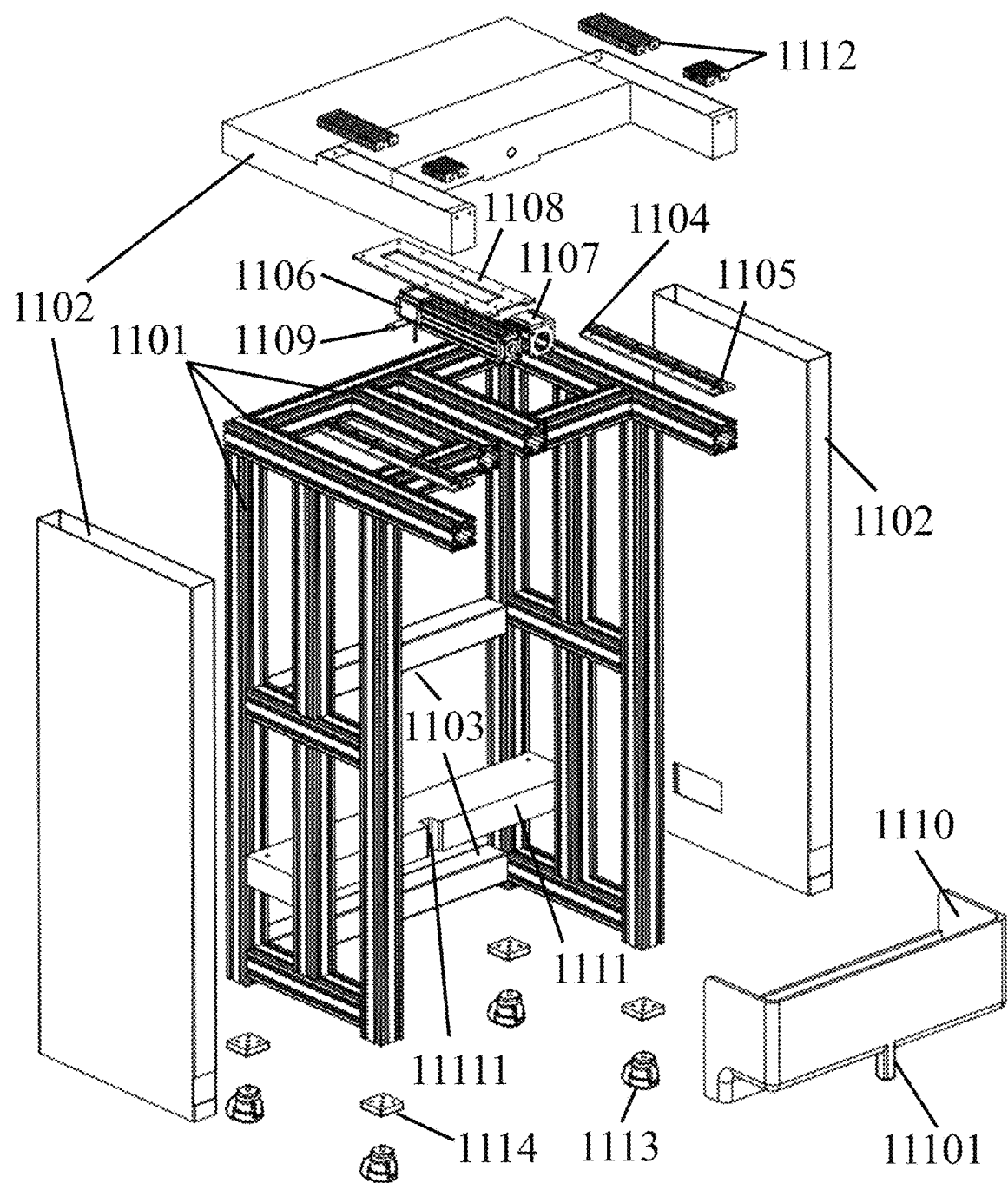
FIG. 4 is a schematic diagram of a structure of a traction component according to an embodiment of the present invention.

As shown in FIG. 4, the traction component 11 comprises a support frame 1101, and the side and top end of the support frame 1101 are provided with a support frame sheet metal 1102. The bottom end of the support frame 1101 is connected to a caster 1113 through a hole flat connector 1114. The support frame 1101 is provided with a motor support plate 1109, and the motor support plate 1109 is provided with a traction push rod 1106. The two sides of the traction push rod 1106 are provided with a traction guide rail 1105, there are two traction guide rails 1105, and the traction guide rail 1105 is connected to the support frame 1101 through a guide rail mounting plate 1104. The traction push rod 1106 is connected to a push rod mounting frame 1108 through a push rod bracket 1107, the push rod mounting frame 1108 is fixed on the support frame 1101. A support frame sheet metal 1102 is provided with a sheet metal groove 11021, and a traction organ cover 1112 is mounted in the sheet metal groove 11021, the support frame sheet metal 1102 plays a protective role in its internal structure, and the traction organ cover 1112 plays a beautiful and protective role without affecting the relative motion of the components. The support frame 1101 is provided with a cross-bed connecting rod 1103 and a counterweight block 1111, the counterweight block 1111 is provided with a storage box 1110, and the storage box 1110 is connected to the counterweight block 1111 through a bulge 11101. There are two cross-bed connecting rods 1103, one of the cross-bed connecting rod 1103 is arranged below the counterweight block 1111, and the storage box 1110 is placed above the counterweight block 1111 and in contact with the below cross-bed connecting rod 1103, another cross-bed connecting rod 1103 is arranged above the counterweight block 1111 and can be used as the robot's push-pull handle. The counterweight block 1111 is provided with a storage groove 11111 suitable for the bulge 11101, and the bulge 11101 is inserted in the storage groove 11111. The bulge 11101 can facilitate the installation and disassembly of storage box 1110 and can limit the storage box's relative motion. The storage box 1110 is placed on the counterweight block 1111, and the counterweight block 1111 plays a supporting role in the storage box 1110.

Figure 5:
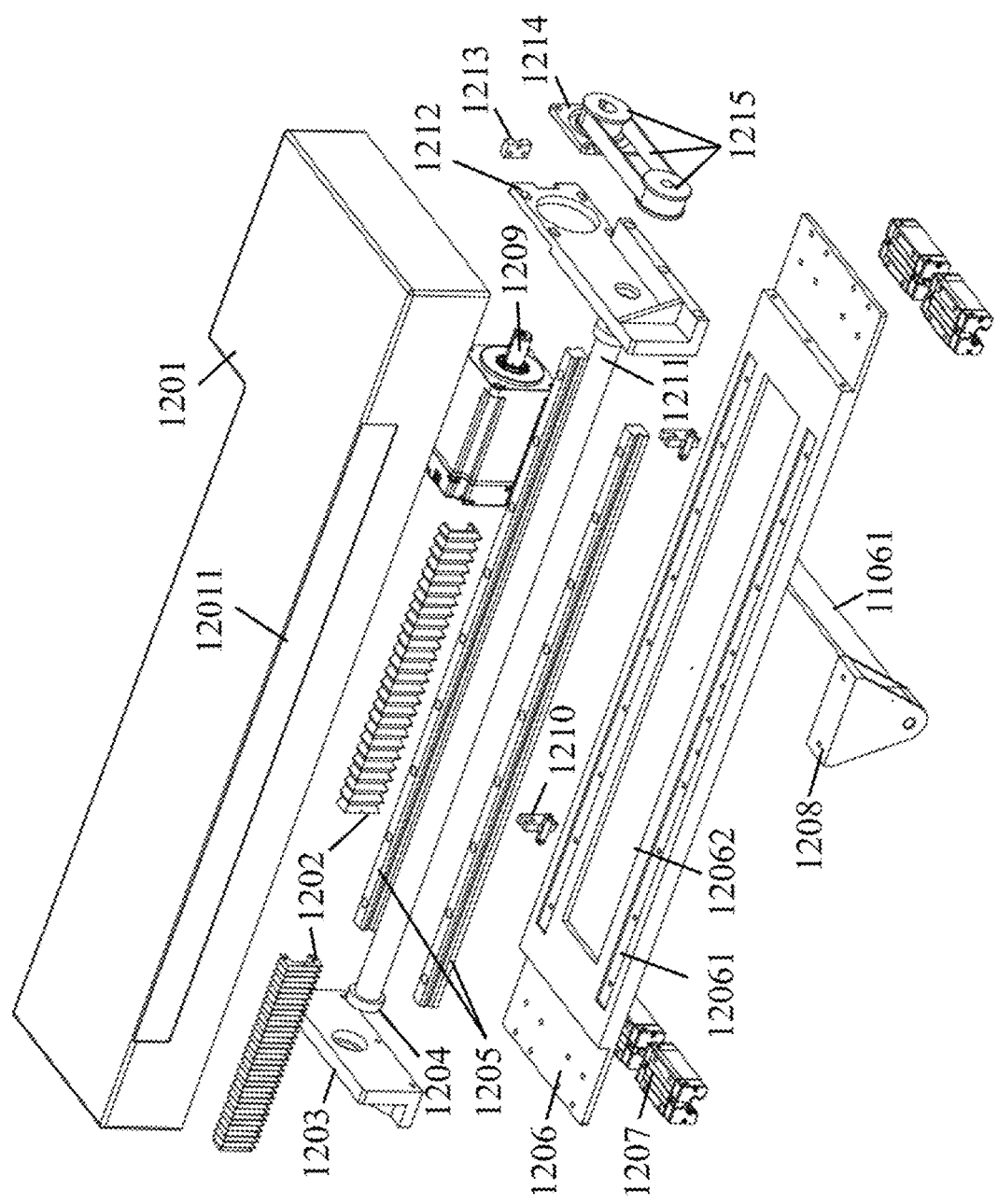
FIG. 5 is a schematic diagram of a structure of a translation component according to an embodiment of the present invention.

As shown in FIG. 5, the translation component 12 comprises a translation bottom plate 1206, the bottom of the translation bottom plate 1206 is provided with a module connector 1208, a movable rod 11061 of the traction push rod 1106 is connected to the module connector 1208. The bottom of the translation bottom plate 1206 is provided with a traction slider 1207, and the traction slider 1207 is slidably connected to the traction guide rail 1105. By pulling the movable rod 11061 of the traction push rod 1106, the module connector 1208 can be driven to move, and then the whole translation component 12 can be driven to move. The traction push rod 1106 stroke is not less than 100 mm, which can ensure that the traction stroke meets the needs of all kinds of fracture reduction. The top of the translation bottom plate 1206 is covered with a translation sheet metal 1201, and the translation sheet metal 1201 is provided with a translation groove 12011, a translation organ cover 1202 is mounted at the translation groove 12011, the translation organ cover 1202 plays a beautiful and protective role without affecting the relative motion of the components. The two ends of the translation bottom plate 1206 are respectively provided with a translation side plate 1203 and a translation motor plate 1212, a translation screw 1211 is arranged between the translation side plate 1203 and the translation motor plate 1212. The two ends of the translation screw 1211 are respectively connected to the translation side plate 1203 and the translation motor plate 1212 through a translation bearing 1204. Both sides of the translation screw 1211 are provided with a translation guide rail 1205, the translation bottom plate 1206 is provided with a guide rail groove 12061, the guide rail groove 12061 is suitable for the translation guide rail 1205, and the translation guide rail 1205 is mounted in the guide rail groove 12061. The output shaft of the translation motor 1209 is connected to one end of the translation screw 1211 through a translation synchronous belt component 1215. The translation motor plate 1212 is provided with the translation motor 1209, and the other side of the translation motor plate 1212 is provided with a translation tensioning plate 1214, and the installation holes of the translation motor 1209 and the translation tensioning plate 1214 are concentric, both of them can move left and right relative to the translation motor plate 1212, during the installation, the bolts pass through the translation motor 1209, the translation motor plate 1212, the translation tensioning plate 1214 in turn and realize the connection of the three by nut locking. One side of the translation motor plate 1212 is fixed with a tensioning bulge 1213 for the tensioning of the translation synchronous belt component 1215, the tensioning bulge 1213 is threadedly connected to the translation tensioning plate 1214 through a single bolt, when is tensioning, the nuts of the locking translation motor 1209, translation motor plate 1212 and translation tensioning plate 1214 are loosened, by adjusting the tension of the tensioning bulge 1213, the screw pair rotates and drags the translation tensioning plate 1214 to move, and then drags the translation motor 1209 to move to realize the tension of the translation synchronous belt assembly 1215. The translation bottom plate 1206 is provided with a translation limit part 1210 for translation limit. The translation bottom plate 1206 is provided with a relief groove 12062, the relief groove 12062 can reduce the weight of the translation component 12, the translation screw 1211 is arranged above the relief groove 12062, the relief groove 12062 can also reduce the overall height of the translation component 12.

Figure 6:
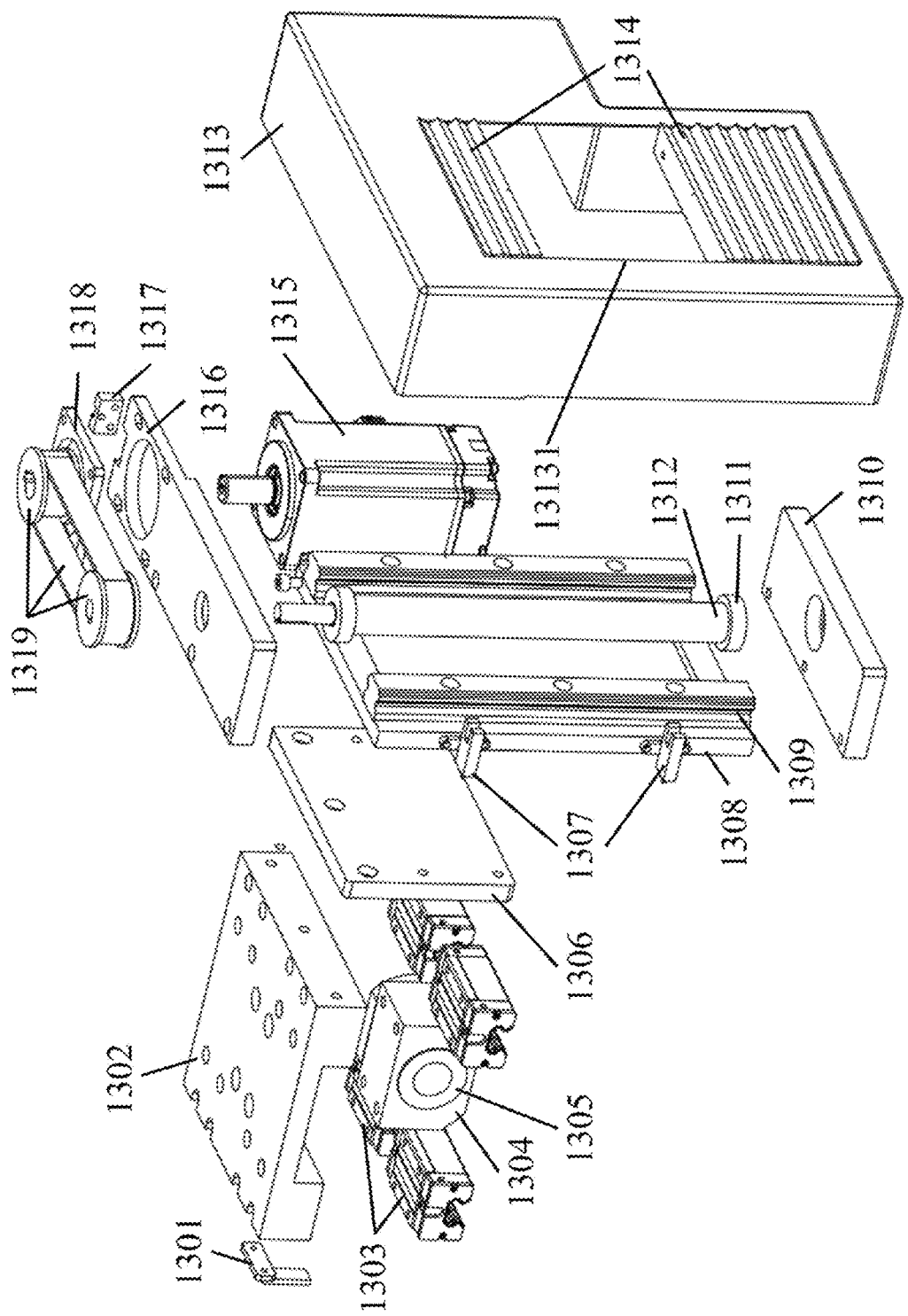
FIG. 6 is a schematic diagram of a structure of a lifting component according to an embodiment of the present invention.

As shown in FIG. 6, the lifting component 13 comprises a lifting bottom plate 1308, and the lifting bottom plate 1308 is connected to a translation slide 1302 through a slide side plate 1306. The bottom end of the translation slide 1302 is provided with a connecting seat 1304 and a translation slider 1303, the translation slider 1303 is arranged on both sides of the connecting seat 1304, and the translation slider 1303 is slidably connected to the translation guide rail 1205. The connecting seat 1304 is provided with a screw nut 1305, the screw nut 1305 is sleeved on the translation screw 1211 and rotationally connected to the translation screw 1211. The translation slide 1302 is provided with a translation baffle 1301 for the translation limit. The translation motor 1209 can drive the translation screw 1211 to rotate through the translation synchronous belt component 1215, and then drive the whole lifting component 13 to translate along the translation guide rail 1205 through the connecting seat 1304 and the translation slider 1303. When translating, the translation baffle 1301 triggers the translation limit part 1210 to interrupt the signal to limit its motion, while ensuring that the robot parts do not interfere with the collision, the translation motion does not exceed the limit of the human fracture site, so as to ensure safety. The translation motion stroke is not less than 400 mm to adapt to the span of the left and right legs of the human body, the stroke is not less than 50 mm during the unilateral leg reduction process, which can ensure that the translation stroke meets the needs of various types of fracture reduction. The upper of the lifting bottom plate 1308 is covered with a lifting sheet metal 1313, the lifting sheet metal is provided with a lifting groove 13131, and the lifting organ cover 1314 is mounted at the lifting groove 13131, the lifting organ cover 1314 plays a beautiful and protective role without affecting the relative motion of the components. Both ends of the lifting bottom plate 1308 are provided with a lifting side plate 1310 and a lifting motor plate 1316, a lifting screw 1312 is arranged between the lifting side plate 1310 and the lifting motor plate 1316. The two ends of the lifting screw 1312 are respectively connected to the lifting side plate 1310 and the lifting motor plate 1316 through a lifting bearing 1311. Both sides of the lifting screw 1312 are provided with a lifting guide rail 1309, and the lifting guide rail 1309 is arranged on the lifting bottom plate 1308. The lifting motor plate 1316 is provided with a lifting motor 1315, and the output shaft of the lifting motor 1315 is in transmission connection with one end of the lifting screw 1312 through the lifting synchronous belt component 1319. One side of the lifting motor plate 1316 is fixed with a lifting bulge 1317 for the tensioning of the lifting synchronous belt component 1319, the lifting bulge 1317 is connected to a lifting tensioning plate 1318 through a single bolt, its tensioning principle is the same as that of the translation synchronous belt assembly 1215. The lifting bottom plate 1308 is provided with a lifting limit part 1307 for lifting limit.

Figure 7:
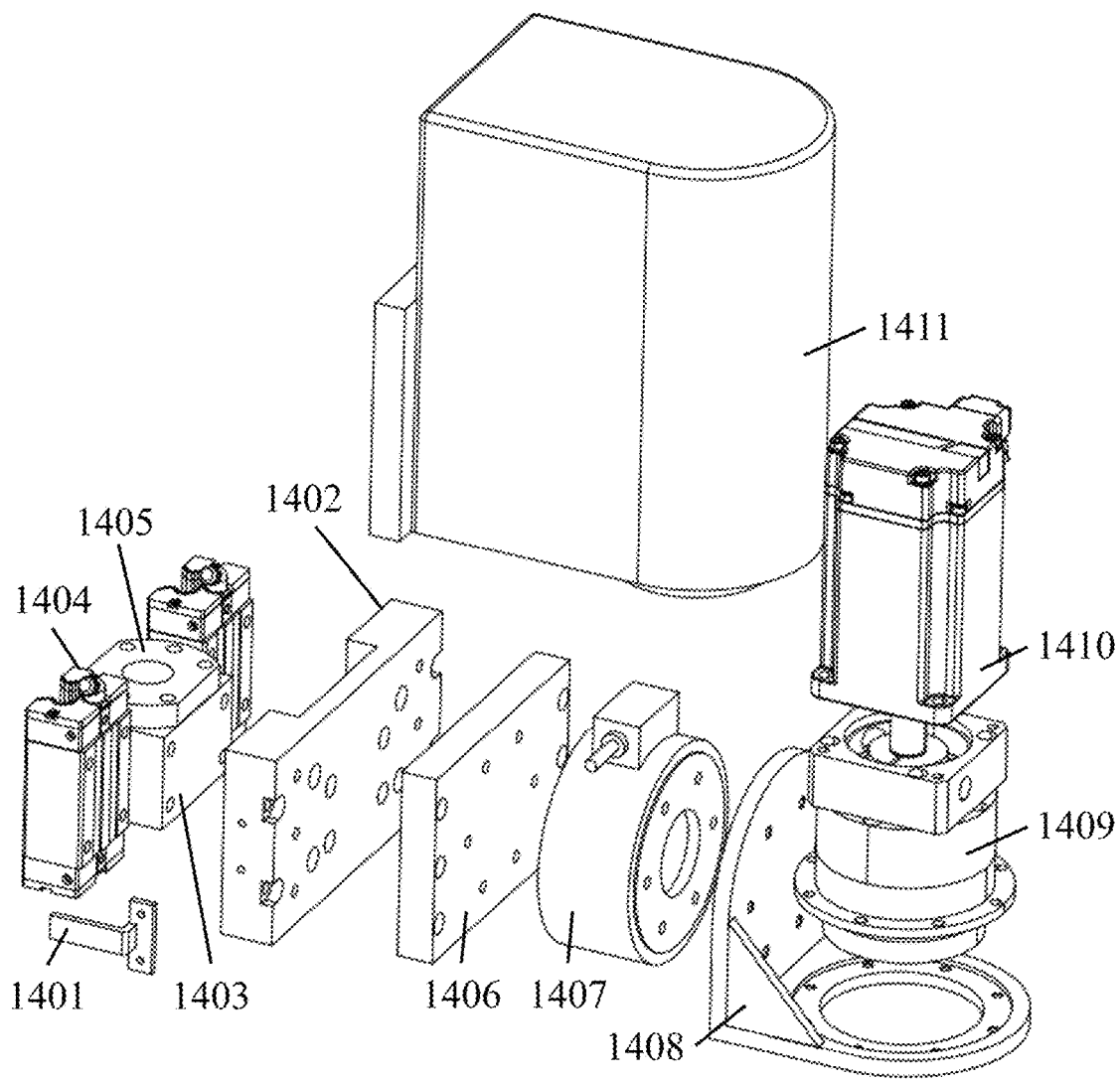
FIG. 7 is a schematic diagram of a structure of a swing component according to an embodiment of the present invention.

As shown in FIG. 7, the swing component 14 comprises a sensor fixed plate 1406, the sensor fixed plate 1406 is connected to a lifting seat 1403 through a lifting slide 1402. The lifting seat 1403 is provided with a lifting nut 1405, the lifting nut 1405 is sleeved on the lifting screw 1312 and is rotatably connected to the lifting screw 1312. The two sides of the lifting seat 1403 are provided with a lifting slider 1404, one side of the lifting slider 1404 is connected to a lifting slide 1402, and the other side of the lifting slider 1404 is slidably connected to the lifting guide rail 1309. The lifting slide 1402 is provided with a lifting baffle 1401 for the lifting limit. The lifting motor 1315 drives the lifting screw 1312 to rotate through the lifting synchronous belt component 1319, and then drives the swing component 14 to lift along the lifting guide rail 1309 through the lifting seat 1403 and the lifting slider 1404. When lifting, the lifting baffle 1401 triggers the lifting limit part 1307 to limit its motion, while ensuring that the robot parts do not interfere with the collision, and the translation motion does not exceed the limit of the human fracture site, so as to ensure safety. The lifting motion stroke is not less than 50 mm, which can ensure that the stroke perpendicular to the bed surface meets the needs of all kinds of fracture reduction. The sensor fixed plate 1406 is provided with a sensor 1407, the sensor 1407 is a six-dimensional force/torque sensor, its axis is parallel to the axis of the bone, and the range of the traction direction is ≥500N, which can meet the traction needs of different patients 4 to overcome muscle antagonistic forces, meanwhile, the sensor 1407 can be used for force feedback control, so as to ensure that the reduction force generated by the robot during the operation does not exceed the limit of human tissue and ensure the safety of the operation. The sensor 1407 is connected to a sensor adapter plate 1408, the sensor adapter plate 1408 is provided with a swing reducer 1409, and the swing reducer 1409 is connected to the output shaft of a swing motor 1410. The lifting slide 1402 is connected to a swing sheet metal 1411, and the swing sheet metal 1411 is covered on the sensor fixed plate 1406, sensor 1407, sensor adapter plate 1408, swing reducer 1409, and swing motor 1410.

Figure 8:
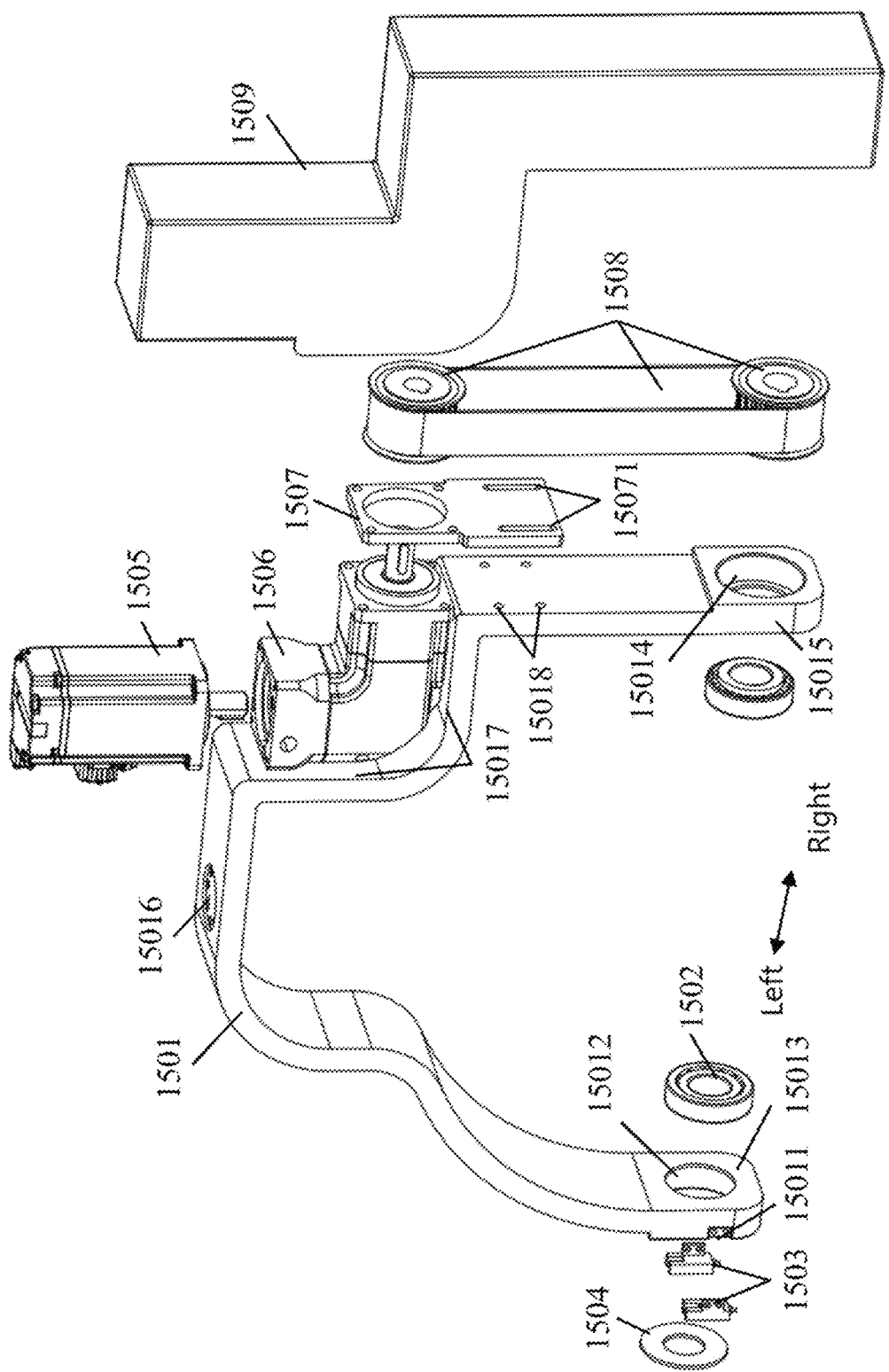
FIG. 8 is a schematic diagram of a structure of a flipping component according to an embodiment of the present invention.
Figure 9:
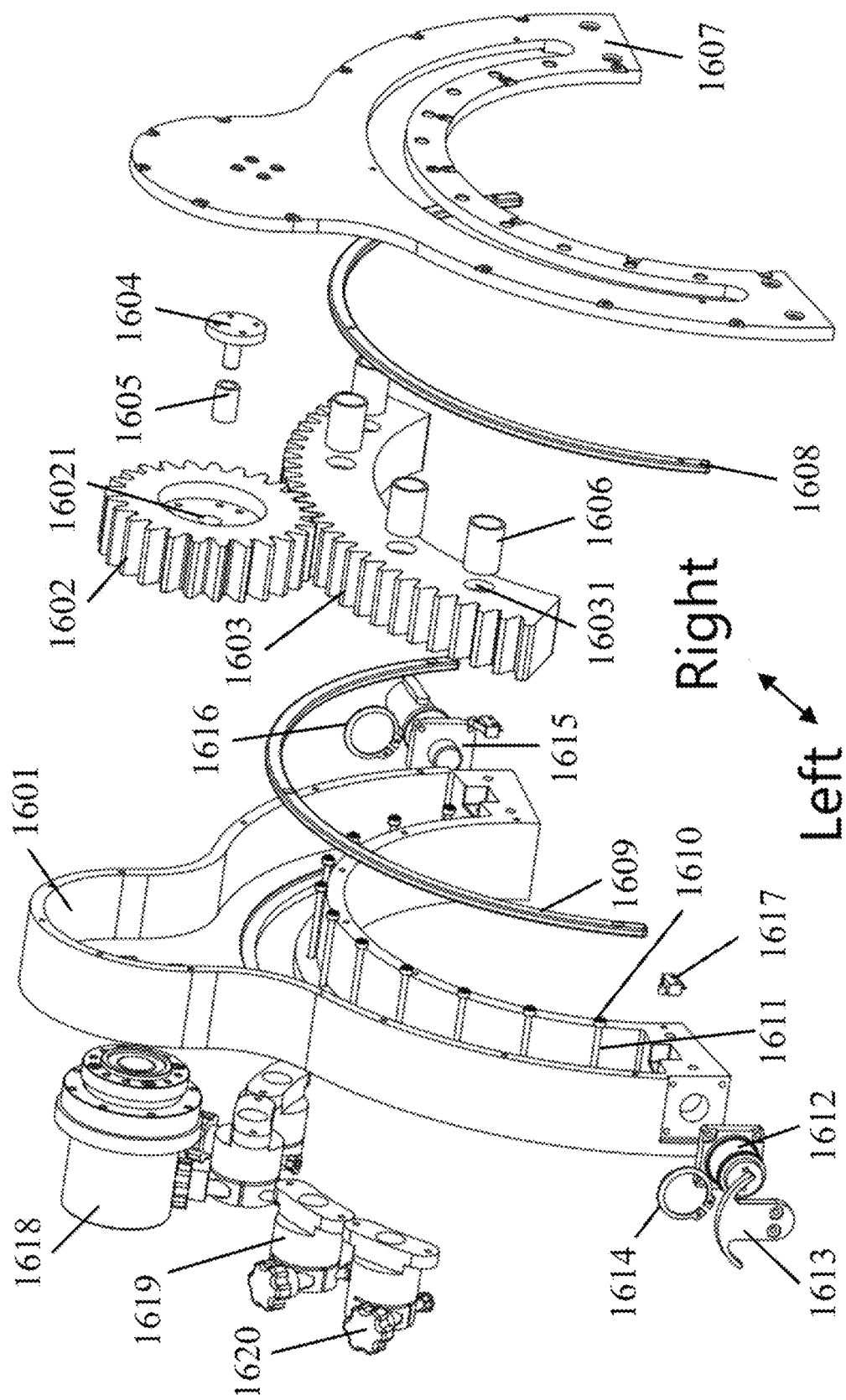
FIG. 9 is a schematic diagram of a structure of a self-rotating component according to an embodiment of the present invention.
Figure 10:
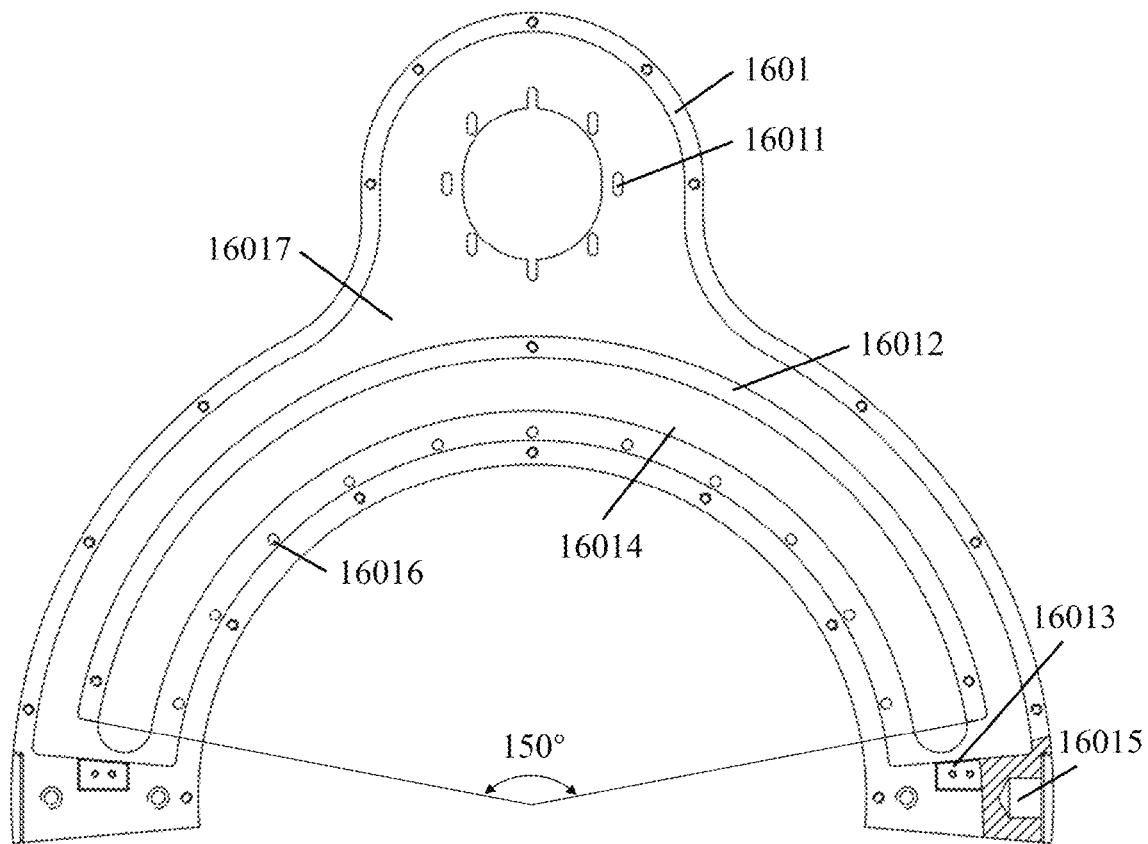
FIG. 10 is a schematic diagram of a structure of a gearbox according to an embodiment of the present invention.
Figure 11:
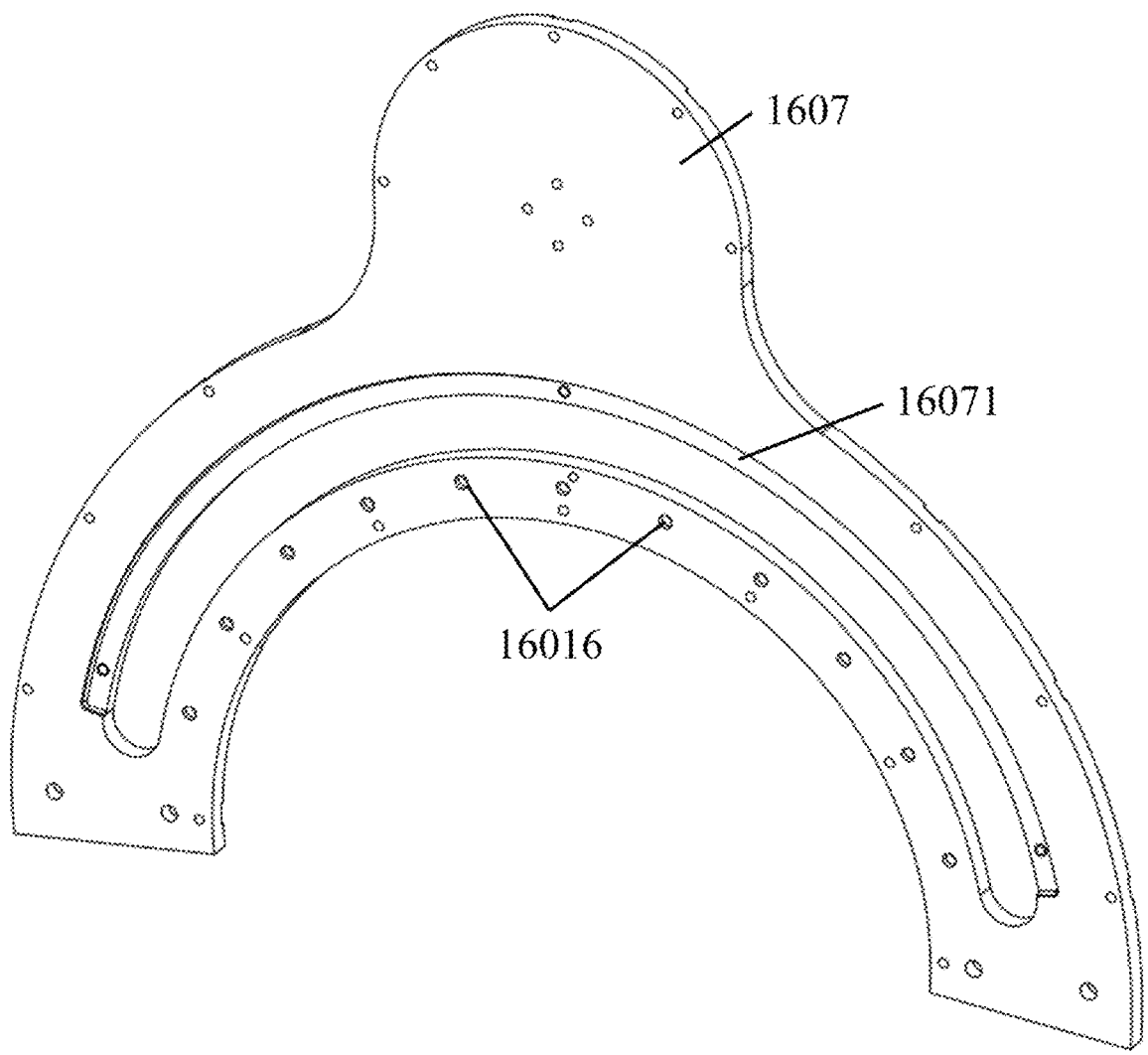
FIG. 11 is a schematic diagram of a structure of a front cover plate according to an embodiment of the present invention.
Figure 12:
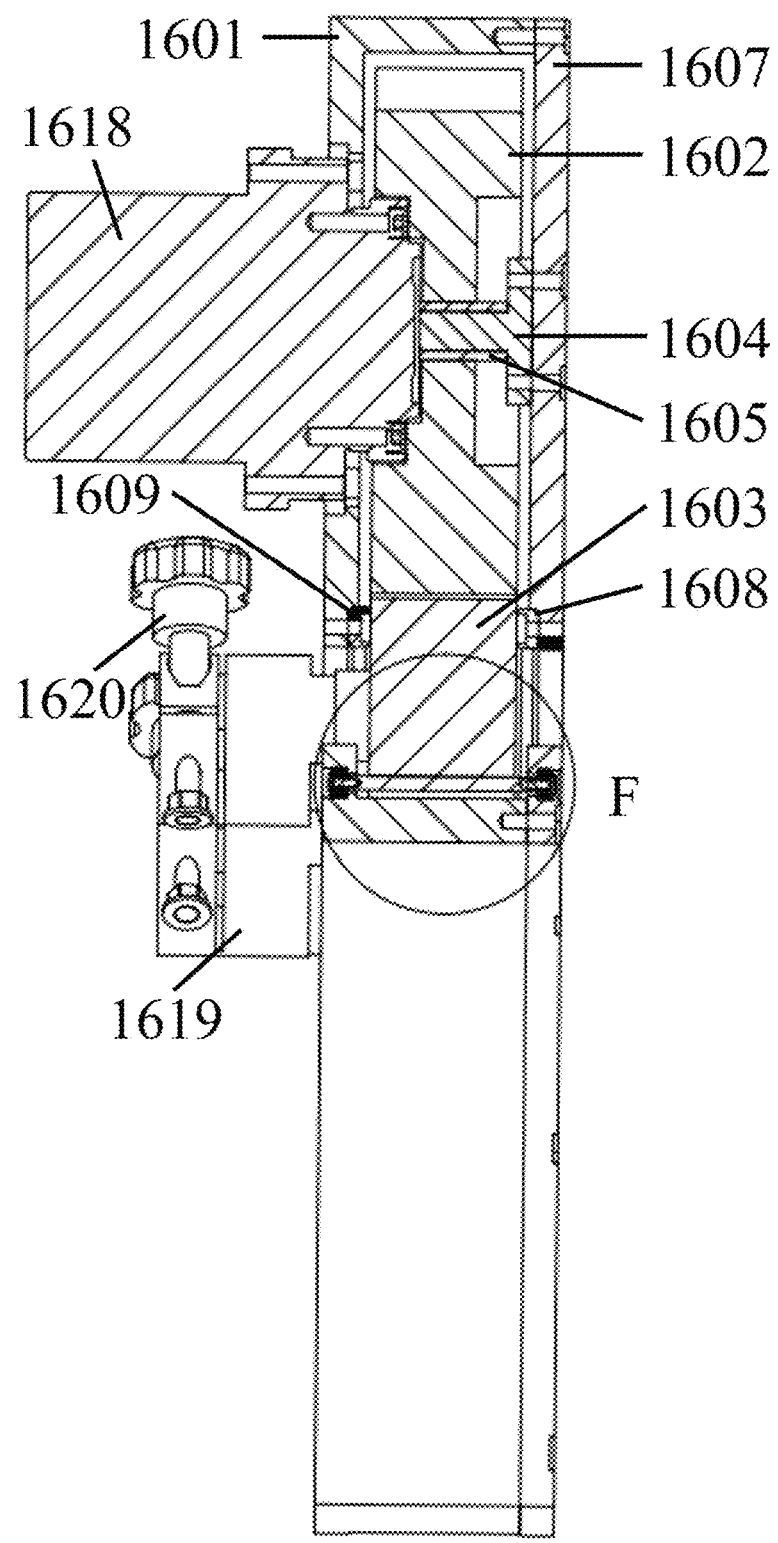
FIG. 12 is a cross-sectional view of a structure of a self-rotating component according to an embodiment of the present invention.
Figure 13:
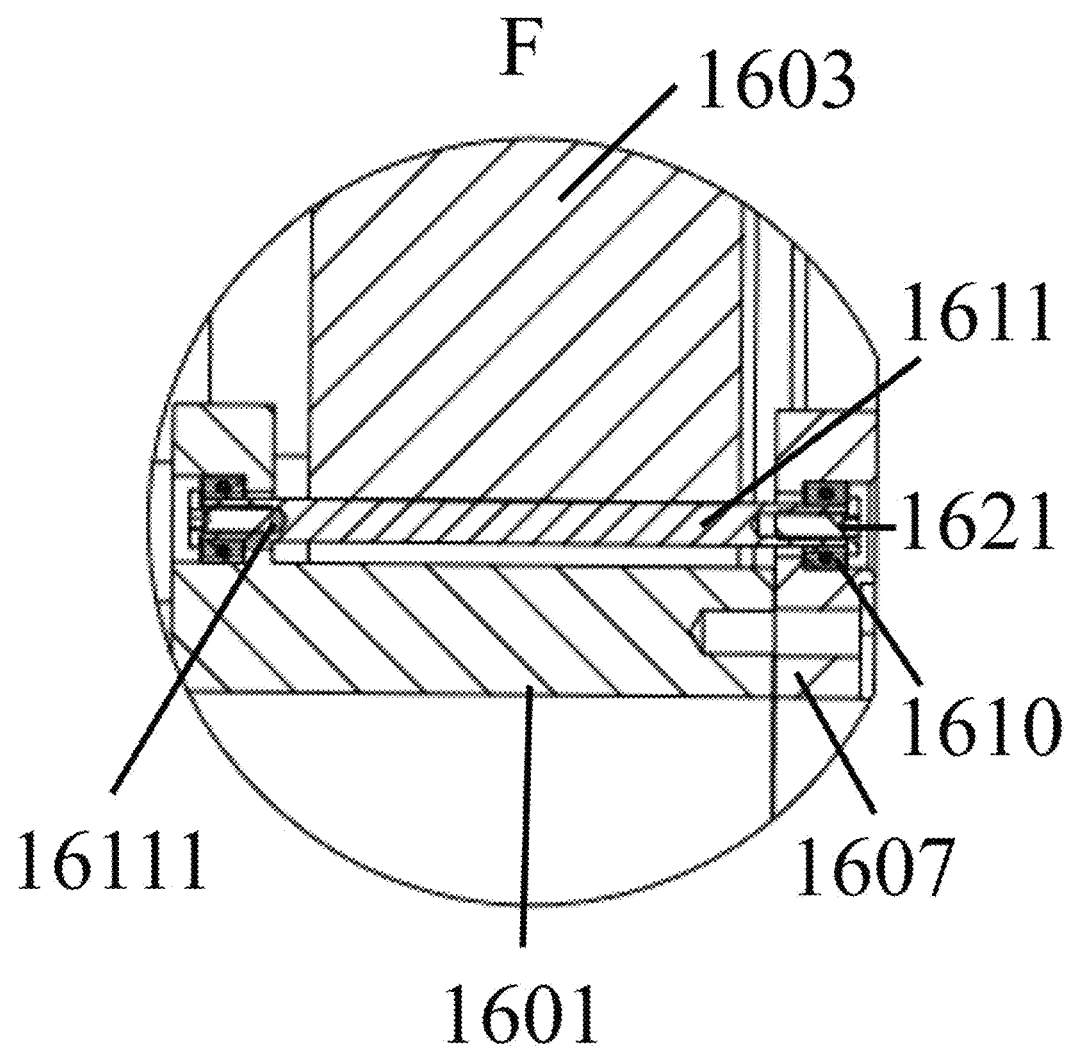
FIG. 13 is an enlarged partial cross-sectional view of a structure of a self-rotating component according to an embodiment of the present invention.

As shown in FIG. 8, the flipping component 15 comprises a support frame 1501, and the upper of the support frame 1501 is covered with a flipping sheet metal 1509. The support frame 1501 is provided with an array hole 15016, and the swing reducer 1409 is connected to the support frame 1501 through an array hole 15016. The swing motor 1410 drives the support frame 1501 to swing through the swing reducer 1409, and then drives the whole flipping component 15 to swing. When swinging, the rotation angle is not less than 30°, which can ensure that the correction angle of angular displacement parallel to the bed surface meets the needs of all kinds of fracture reduction. One end of the support frame 1501 is provided with a left lug 15013 with a left groove 15012 and an installation groove 15011, and the other end of the support frame 1501 is provided with a right lug 15015 with a right groove 15014. The left groove 15012 and the right groove 15014 are respectively provided with a flipping bearing 1502. The end of the left lug 15013 is provided with a rubber pad 1504, which plays a sealing role. The left lug 15013 is provided with a flipping limit part 1503 for limiting the flipping limit, the support frame 1501 is provided with a step surface 15017, the step surface 15017 is provided with a flipping reducer 1506, this arrangement can reduce the size along the width direction. The flipping reducer 1506 is connected to the output shaft of a flipping motor 1505, and the flipping reducer 1506 is in transmission connection with a flipping synchronous belt component 1508. A flipping motor plate 1507 is arranged between the flipping reducer 1506 and the flipping synchronous belt component 1508, the flipping motor plate 1507 is provided with a straight groove 15071 for adjusting the tension of the flipping synchronous belt component 1508. The straight groove 15071 is provided with an installation hole 15018, and the installation hole 15018 is arranged on the support frame 1501. The straight groove 15071 is connected to the installation hole 15018 through an adjusting bolt, loosening the bolt, by adjusting the position of the upper and lower installation holes 15018 on the straight groove 15071, the distance between the output shaft of the flipping reducer 1506 and the right shaft 1615 can be changed, and then the tension of the flipping synchronous belt assembly 1508 can be realized.

As shown in FIG. 9, FIG. 10, FIG. 11, FIG. 12, and FIG. 13, the self-rotating component 16 comprises a gearbox 1601, and the two ends of the gearbox 1601 are respectively provided with a left shaft 1612 and a right shaft 1615. The gearbox 1601 is connected to the flipping bearing 1502 of the left groove 15012 of the support frame 1501 through the left shaft 1612, the left shaft 1612 is provided with a left shaft snap ring 1614 and a flipping baffle 1613 for the flipping limit. The gearbox 1601 is connected to the flipping bearing 1502 of the right groove 15014 of the support frame 1501 through the right shaft 1615, the right shaft 1615 is provided with a right shaft snap ring 1616, and the right shaft 1615 passes through the right groove 15014 of the support frame 1501 and is in transmission connection with to the flipping synchronous belt component 1508. The left shaft 1612 and the right shaft 1615 are inserted into a shaft hole 16015 at both ends of the gearbox 1601 to strengthen the connection and guidance. The flipping motor 1505 drives the gearbox 1601 to flip on the support frame 1501 by flipping the flipping reducer 1506 and flipping synchronous belt component 1508, and then drives the whole self-rotating component 16 to flip. When the self-rotating component 16 rotates back and forth along the left shaft 1612 axis, the flipping baffle 1613 triggers the flipping limit part 1503 to limit its motion, while ensuring that the robot parts do not interfere with the collision, it is ensured that the rotation motion does not exceed the limit of the human fracture site, thereby ensuring safety. When flipping, the rotation angle is not less than 30°, which can ensure that the angle displacement correction angle perpendicular to the bed surface meets the needs of all kinds of fracture reductions. The gearbox 1601 is provided with a front cover plate 1607, the gearbox 1601 is provided with a gear 1602. The outer surface of the gearbox 1601 is provided with a joint motor 1618, the gearbox 1601 is provided with motor installation holes 16011, and the joint motor 1618 is mounted on the gearbox 1601 through the motor installation hole 16011. The output shaft of the joint motor 1618 is connected to gear 1602, the gear 1602 is meshed with a ring gear 1603. The motor installation hole 16011 is a straight groove shape, which can adjust the meshing relationship between gear 1602 and ring gear 1603, facilitate assembly and adjustment, and ensure transmission efficiency. The gear 1602 center is provided with a gear shaft 1604, the gear shaft 1604 is fixed on the front cover plate 1607, the gear shaft 1604 is connected to the center of the gear 1602 through an oil-free bearing 1605, the oil-free bearing 1605 is inserted in a center hole 16021 of the gear 1602, the output shaft of the joint motor 1618 can drive the gear 1602 to rotate on the oil-free bearing 1605. A groove structure 16017 is arranged in the gearbox 1601, and the gear ring 1603 does the circular reciprocating motion along the groove structure 16017 of the gearbox 1601. The ring gear 1603 is slidably connected to the gearbox 1601 through a roller 1611, small bearing holes 16016 are arranged in the gear box, and a roller bearing 1610 is arranged in the small bearing hole 16016, the two ends of the roller 1611 are rotationally connected to the gearbox 1601 through the roller bearing 1610. Both ends of the roller 1611 are provided with threaded holes, and a limit screw 1621 is mounted in the threaded hole. A rear insert strip 1609 is arranged between one side of the ring gear 1603 and the gearbox 1601, and a front insert strip 1608 is arranged between the other side of the ring gear 1603 and the front cover plate 1607. The gearbox 1601 is provided with a rear groove 16012, the rear insert strip 1609 is arranged in the rear groove 16012, the front cover plate 1607 is provided with a front groove 16071, and the front insert strip 1608 is arranged in the front groove 16071. The front insert strip 1608 and the rear insert strip 1609 can limit the collision and friction of the gear ring 1603 with the front cover plate 1607 and the gearbox 1601 during the motion, which can reduce the working noise and working friction, so as to improve the motion performance of the robot. The gearbox 1601 is provided with a self-rotating limit part 1617, and there are two self-rotating limit parts 1617, the two self-rotating limit parts 1617 are respectively provided in two limit grooves 16013 of the gearbox 1601. The angle of center angle of the ring gear 1603 is 110°, the joint motor 1618 can drive the gear 1602 to rotate, and then drive the ring gear 1603 to perform circular reciprocating motion along the groove structure 16017 of gearbox 1601, the ring gear 1603 triggers the self-rotating limit part 1617 to limit its motion, while ensuring that the robot parts do not interfere with the collision, it ensures that the rotation motion does not exceed the limit of the human fracture site, thereby ensuring safety. The ring gear 1603 can ensure that the positive/reverse rotation angle is not less than 45° in the groove structure 16017, which can ensure that the self-rotating correction angle around the bone axis meets the needs of all kinds of fracture reduction. The ring gear 1603 is provided with bearing holes 16031, a linear bearings are arranged in the bearing hole 16031. The gearbox 1601 is provided with a clamping seat 1619, and the clamping seat 1619 is provided with a locking handle 1620. The clamping seat 1619 is fixed on the gear ring 1603 and passes through an arc straight groove 16014 in the gearbox 1601, the center angle of the arc straight groove 16014 is 150°.

Figure 14:
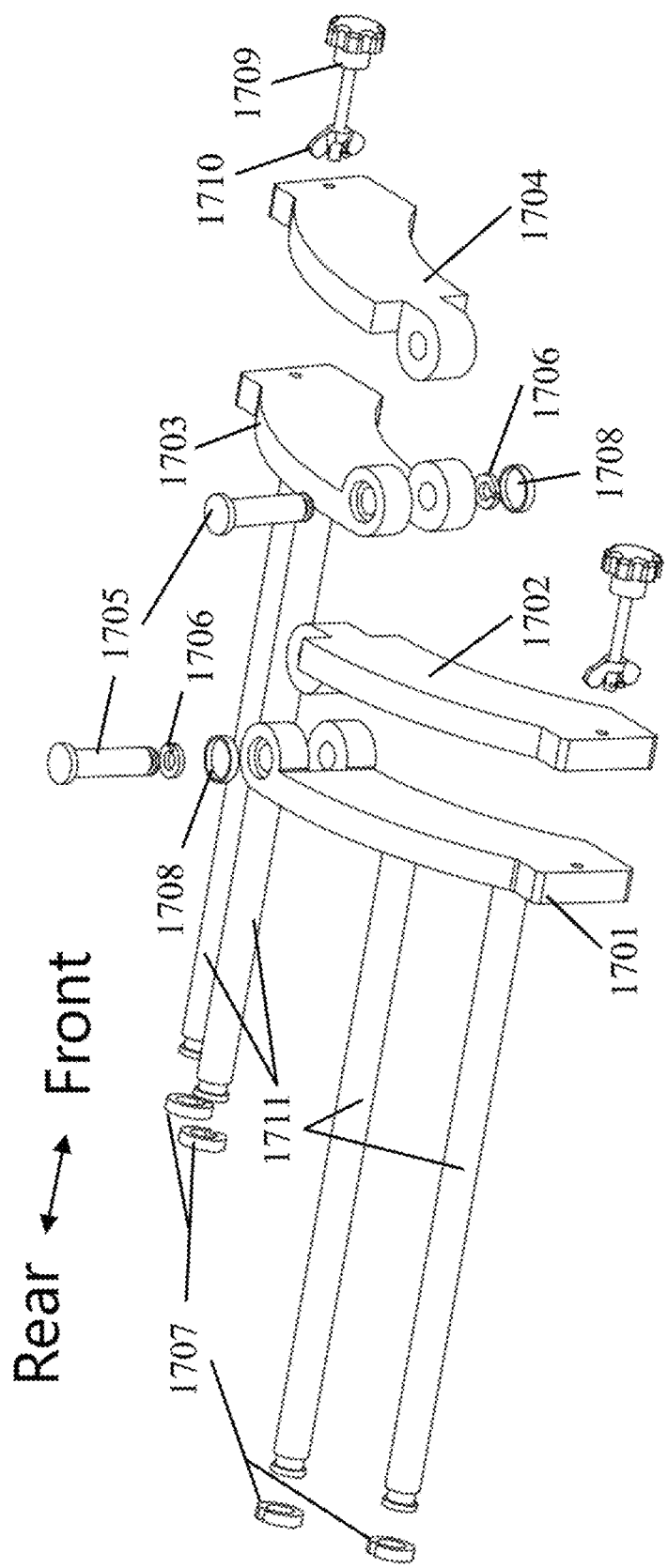
FIG. 14 is a schematic diagram of a structure of a mobile end clamping component according to an embodiment of the present invention.
Figure 15:
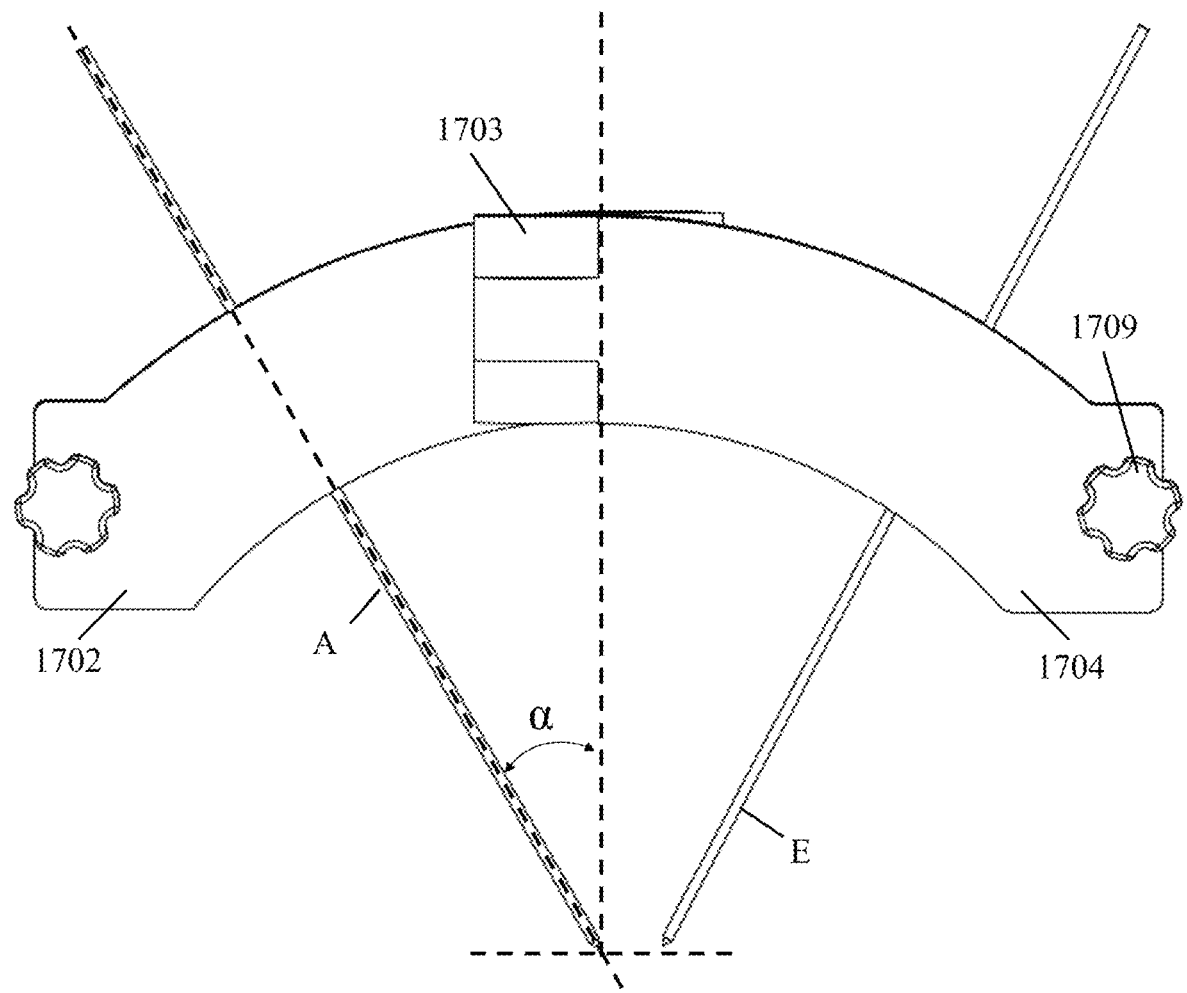
FIG. 15 is a schematic diagram of a clamping state of a Kirschner wire according to an embodiment of the present invention.
Figure 16:
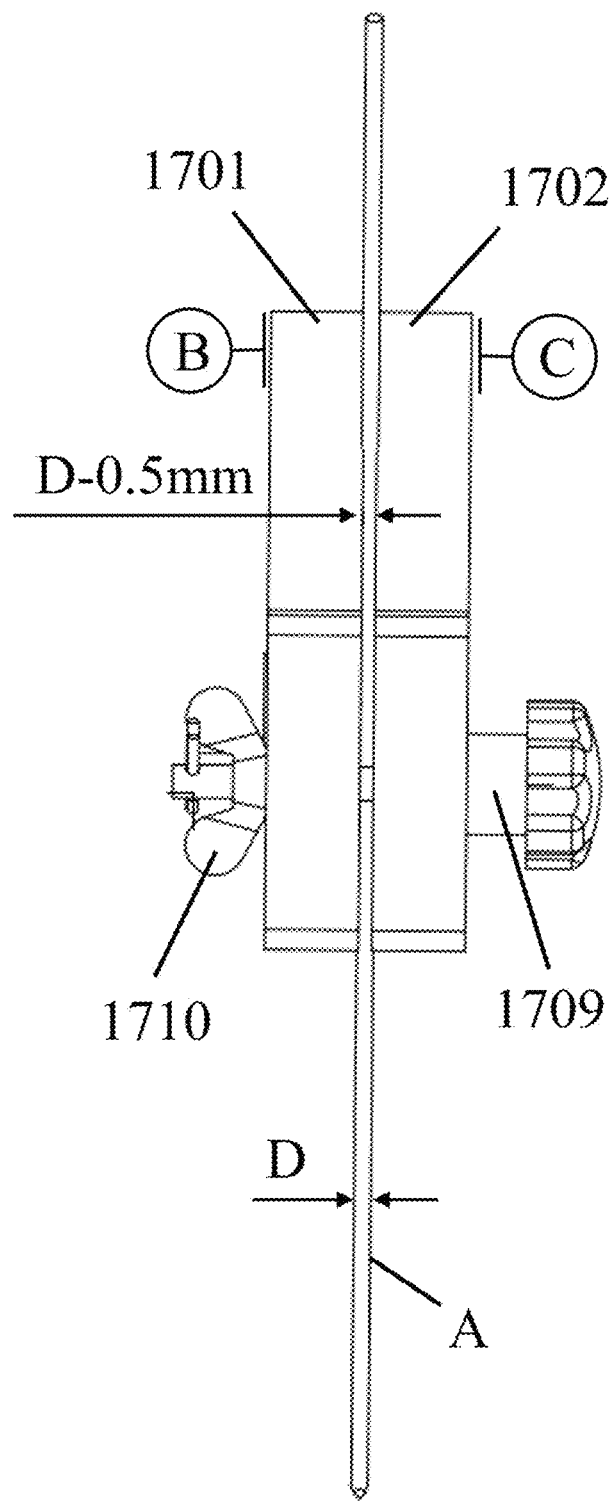
FIG. 16 is an end view of a structure of a Kirschner wire clamping according to an embodiment of the present invention.

As shown in FIG. 14, the mobile end clamping component 17 comprises four optical shafts 1711, four optical shafts 1711 are connected to the ring gear 1603 through the linear bearing 1606, and the optical shaft 1711 is clamped in the clamping seat 1619. The mobile end clamping component 17 is connected to the gear ring 1603 of the gearbox 1601 through the optical shaft 1711, and the joint motor 1618 can drive the mobile end clamping component 17 to perform circular motion. One end of the four optical shafts is provided with a step, and the step is provided with a carbon ring. The other end of the two optical shafts 1711 is connected to a left inner splint 1701, and the other end of the other two optical shafts 1711 is connected to a right inner splint 1703. One end of the left inner splint 1701 is connected to a left outer splint 1702 through a rotating shaft 1705, the other end of the left inner splint 1701 is connected to the left outer splint 1702 through a rotating handle 1709, one end of the right inner splint 1703 is connected to a right outer splint 1704 through the rotating shaft 1705, the other end of the right inner splint 1703 is connected to the right outer splint 1704 through the rotating handle 1709. The top of the rotating shaft 1705 is provided with a boss, and the bottom of the rotating shaft 1705 is provided with a groove, after the rotating shaft 1705 is connected with the inner splints and outer splints, the groove at the bottom of the rotating shaft 1705 is mounted with a shaft ring 1706, and a plug 1708 is mounted at the bottom of the inner splint. The shaft ring 1706 plays the role of axial limit, and the plug 1708 plays the role of sealing. The rotating handle 1709 comprises a head and a rod, rotary holes are arranged on the inner splints and outer splints, and the rod is inserted in the rotary hole and rotationally connected with it, one end away from the head of the rod is provided with a butterfly nut 1710. The left inner splint 1701 and the left outer splint 1702, the right inner splint 1703 and the right outer splint 1704 can rotate relative to the rotating shaft 1705. Taking the left inner splint 1701 and the left outer splint 1702 as an example, as shown in FIGS. 15-16, when rotating, the left outer splint 1702 can press the Kirschner wire A, and the pressing degree of the Kirschner wire A can be adjusted by rotating the head of the rotating handle 1709 and the butterfly nut 1710. The diameter of Kirschner wire A is D, when the outer side of the left inner splint 1701 is parallel to the outer side C of the left outer splint 1702, the distance between the inner side of the left inner splint 1701 and the outer side C of the left outer splint 1702 is less than the diameter D, and the distance is taken as 0.5 mm, this kind of configuration locking can form an interference structure to ensure that Kirschner wire A is fixed firmly. The left inner splint 1701, the left outer splint 1702, the right inner splint 1703, and the right outer splint 1704 are all arc-shaped, so they can hold Kirschner wire A with different angles α along its circumferential direction.

Figure 17:
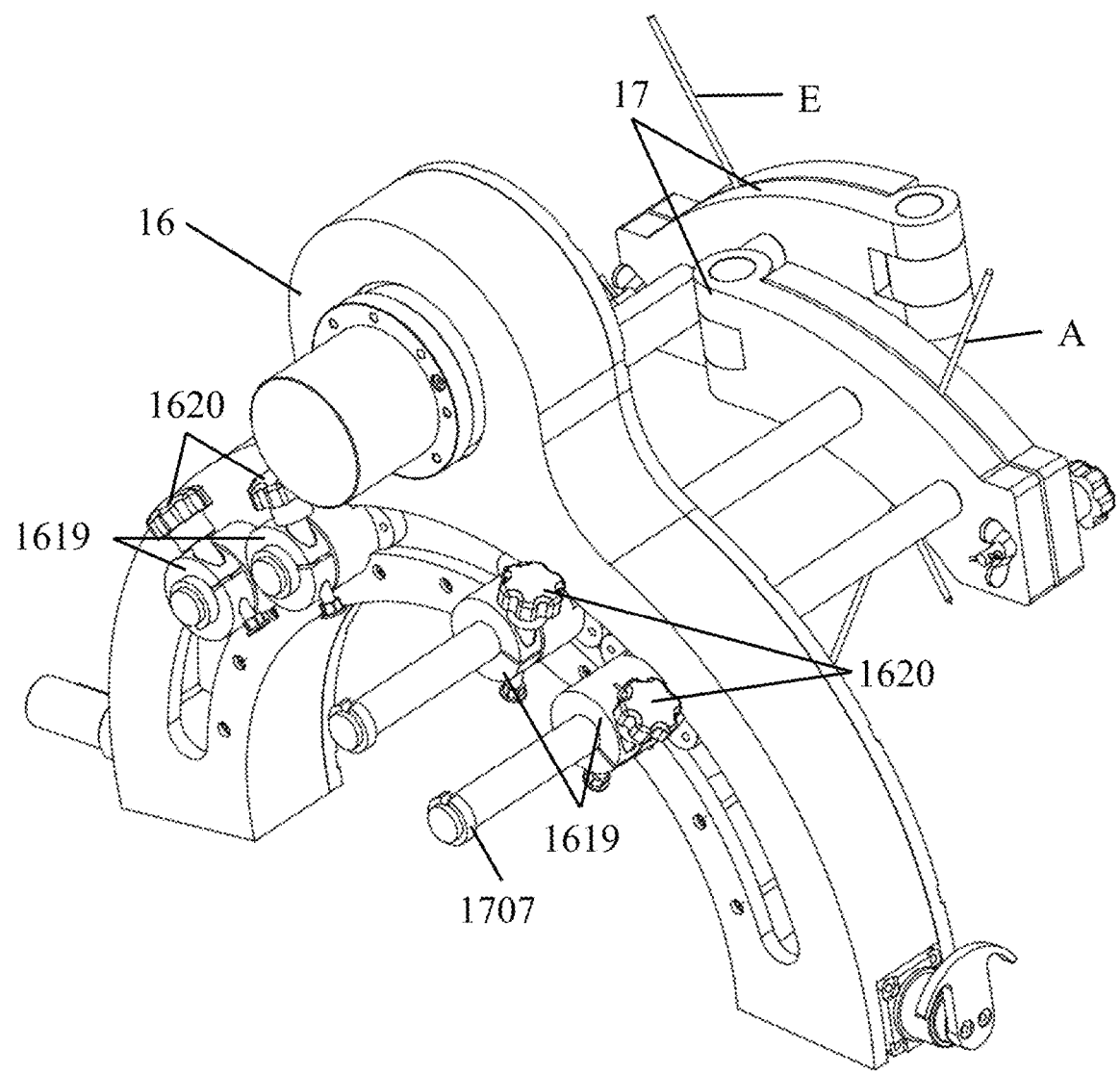
FIG. 17 is a schematic diagram of a connection relationship between a mobile end clamping component and a self-rotating component according to an embodiment of the present invention.

As shown in FIG. 17, the mobile end clamping component 17 is connected to the self-rotating component 16, the optical shaft 1711 passes through the ring gear 1603, the linear bearing 1606, and the clamping seat 1619, by adjusting the locking handle 1620, the clamping seat 1619 can hold tightly the optical shaft 1711, so as to realize the connection between the mobile end clamping component 17 and the self-rotating component 16, the carbon ring 1707 is mounted after the connection, which can prevent the mobile end clamping component 17 from separating from the self-rotating component 16 during working. When working, according to the distance between the two Kirschner wires A and E entered by the doctor along the direction of the optical shaft 1711, the position of the optical shaft 1711 on the clamping seat 1619 can be adjusted to fix two Kirschner wires at the same time. In addition, since the doctor's posture of entering two Kirschner wires is arbitrary, the structure can simultaneously satisfy the fixation of two Kirschner wires E with different distances and postures, so as to improve the applicability and operability of the robot.

Figure 18:
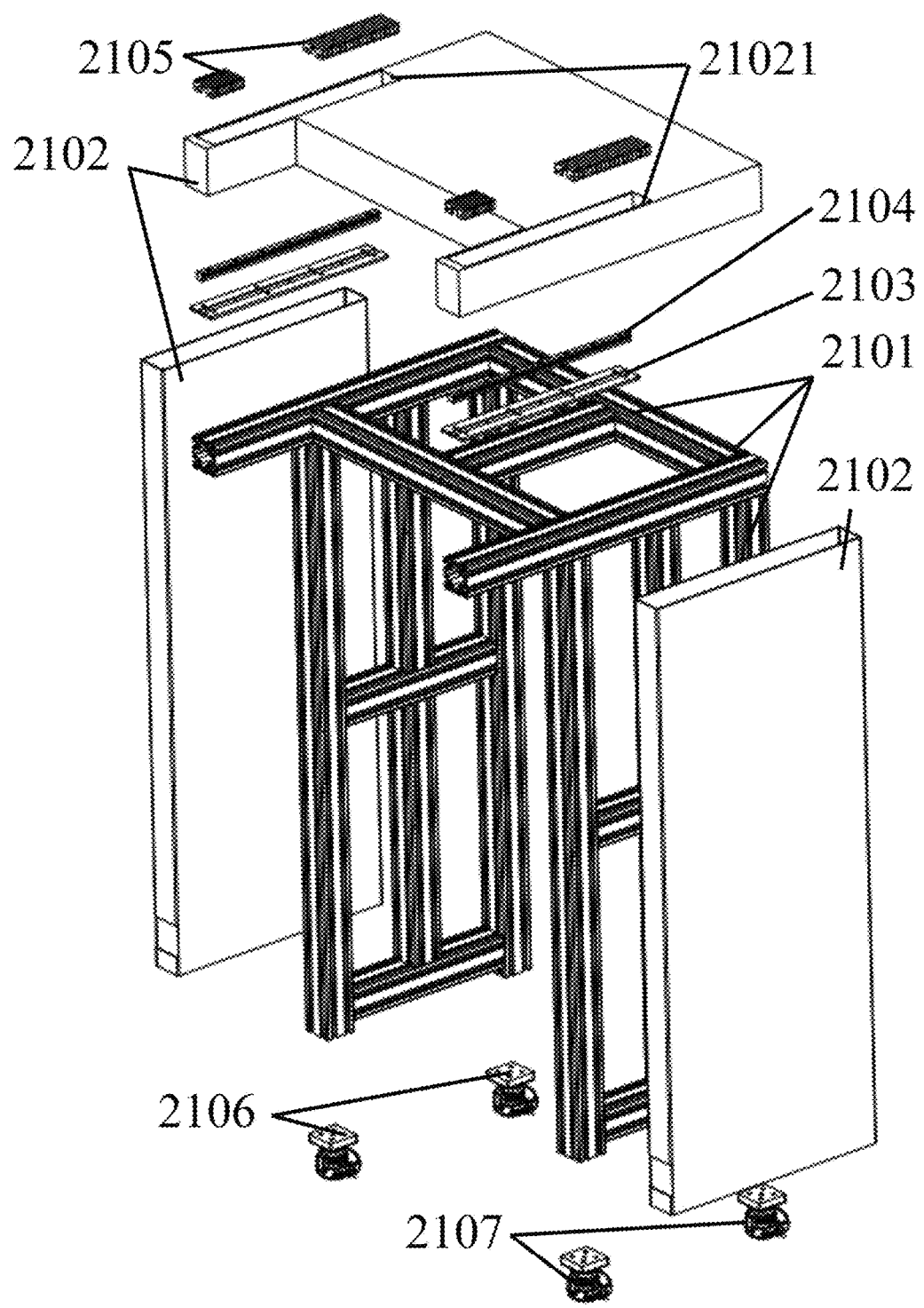
FIG. 18 is a schematic diagram of an auxiliary traction structure according to an embodiment of the present invention.

As shown in FIG. 18, the auxiliary traction structure 21 comprises a fixed frame 2101, both sides and the top of the fixed frame 2101 are provided with a shell 2102. The shell 2102 at the top of the fixed frame 2101 is provided with a rectangular groove 21021, and an organ cover I 2105 is mounted in the rectangular groove 21021, the an organ cover I 2105 plays a beautiful and protective role without affecting the relative motion of the components. The bottom of the fixed frame 2101 is connected to an auxiliary caster 2107 through a connecting plate 2016. The top of the fixed frame 2101 is provided with a fixed plate 2103, the fixed plate 2103 is provided with a guide rail I 2104, and the guide rail I 2104 is arranged in the shell 2102 at the top of the fixed frame 2102.

Figure 19:
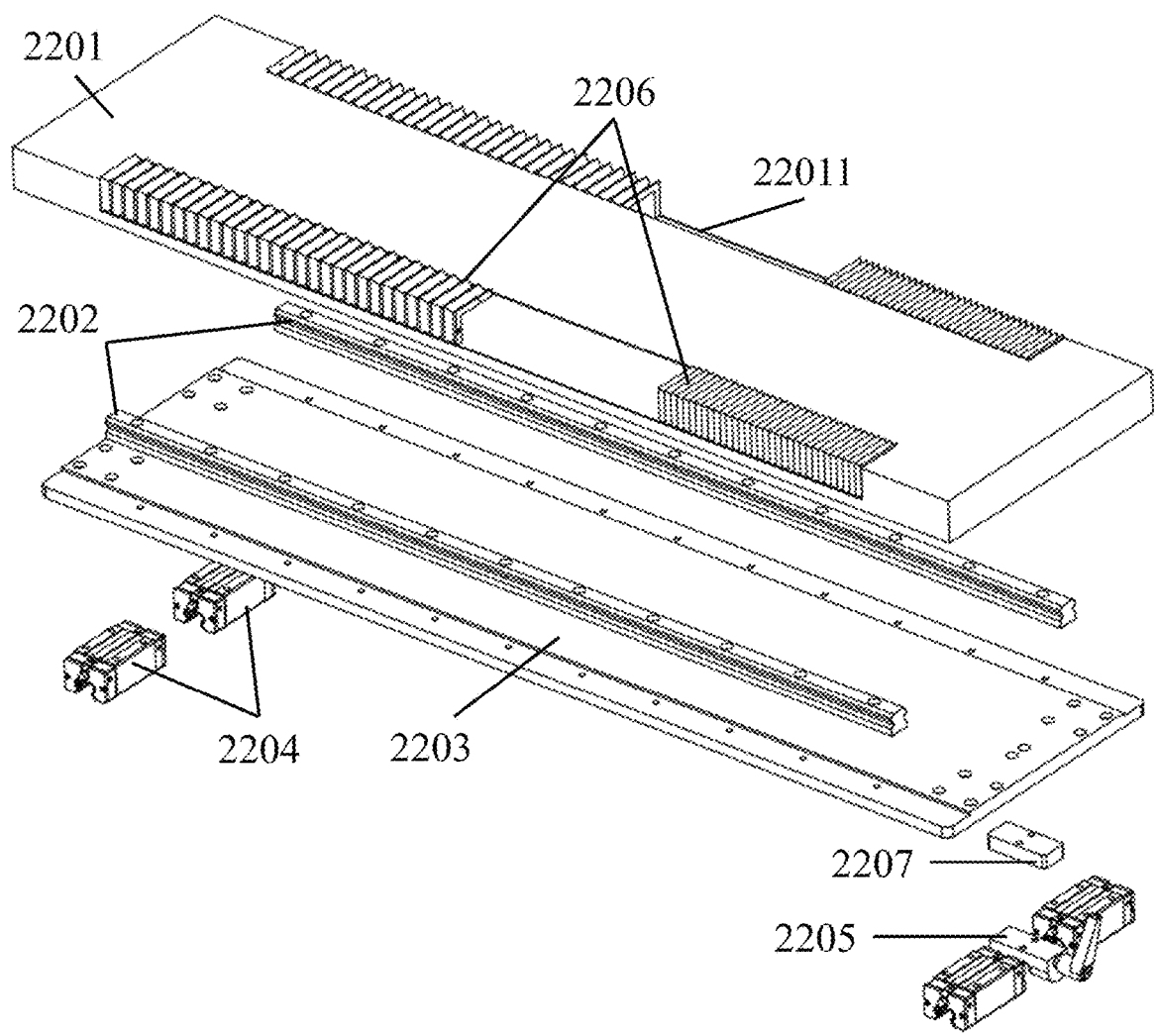
FIG. 19 is a schematic diagram of an auxiliary translation structure according to an embodiment of the present invention.

As shown in FIG. 19, the auxiliary translation structure 22 comprises a bottom plate I 2203, the bottom end of the bottom plate I 2203 is provided with a slider I 2204, and the slider I 2204 is slidably connected to the guide rail I 2104, the bottom end of the bottom plate I 2203 is connected to a traction gripper 2205 through a cushion block I 2207. When using, first adjust the traction gripper 2205 to a loose state, and drag the auxiliary translation structure 22 to move along the guide rail I 2104, when adjusted to the appropriate position, adjust the traction gripper 2205 to a locking state, thereby limiting the relative position of the auxiliary translation structure 22 relatives to the auxiliary traction structure 21. The upper of a connecting bottom plate I 2203 is covered with a rectangular shell 2201, and the rectangular shell 2201 is provided with a long groove 22011, the organ cover II 2206 is mounted in the long groove 22011, the organ cover II 2206 plays a beautiful and protective role without affecting the relative motion of the components. The top of the bottom plate I 2203 is provided with a guide rail II 2202.

Figure 20:
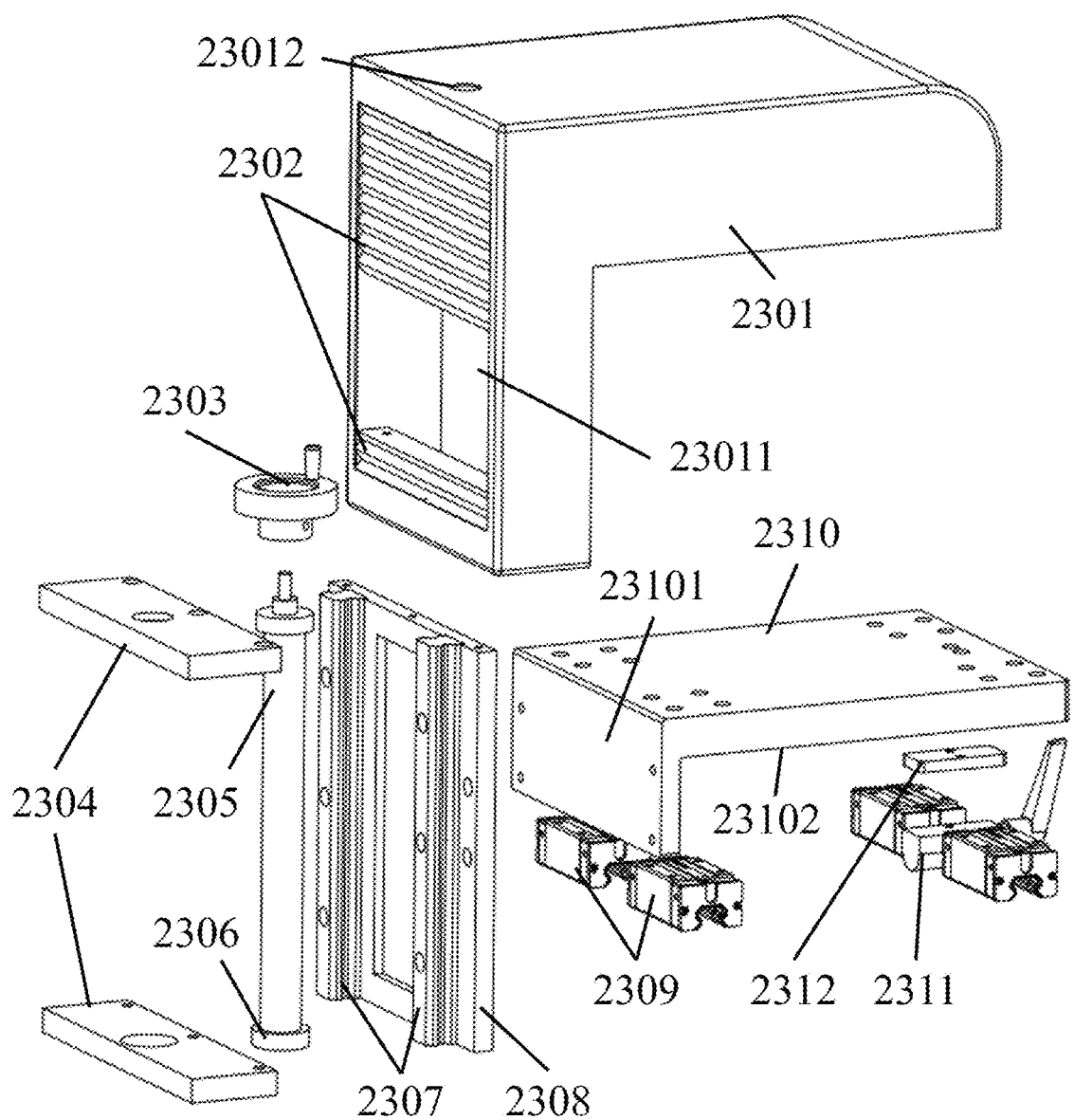
FIG. 20 is a schematic diagram of a hand-cranking lifting structure according to an embodiment of the present invention.

As shown in FIG. 20, the hand-cranking lifting structure 23 comprises a bottom plate II 2308, one side of the bottom plate II 2308 is provided with an L-shaped plate 2310, the bottom end of the L-shaped plate 2310 is provided with a slider II 2309, the slider II 2309 is slidably connected to the guide rail II 2202. A short side 23101 of the L-shaped plate 2310 is fixedly connected with the bottom plate II 2308, and a long side inner side 23102 is connected with the slider II 2309. The bottom end of the L-shaped plate 2310 is connected to a translation gripper 2311 through a cushion block II 2312, when using, first adjust the translation gripper 2311 to a loose state, and the hand-cranking lifting structure 23 is dragged to move along the guide rail II 2202, when adjusted to the appropriate position, the translation gripper 2311 is adjusted to a locking state, thereby limiting the relative position of the hand-cranking lifting structure 23 relatives to the auxiliary translation structure 22. Both ends of the bottom plate II 2308 are provided with a vertical plate 2304, and the other side of the bottom plate II 2308 is provided with a guide rail III 2307 and a screw I 2305. Both ends of the screw I 2305 are connected to the vertical plate 2304 through an auxiliary bearing 2306. An L-shaped shell 2301 is provided with a circular hole 23012, and one end of the screw I 2305 is connected to a handwheel 2303 through the circular hole 23012. The bottom plate II 2308 is connected to the L-shaped shell 2301, the L-shaped shell 2301 is covered on the screw I 2305, the guide rail III 2307 and the L-shaped plate 2310. The L-shaped shell is provided with a short groove 23011, and an organ cover III is mounted in the short groove 23011, which plays a beautiful and protective role without affecting the relative motion of the components.

Figure 21:
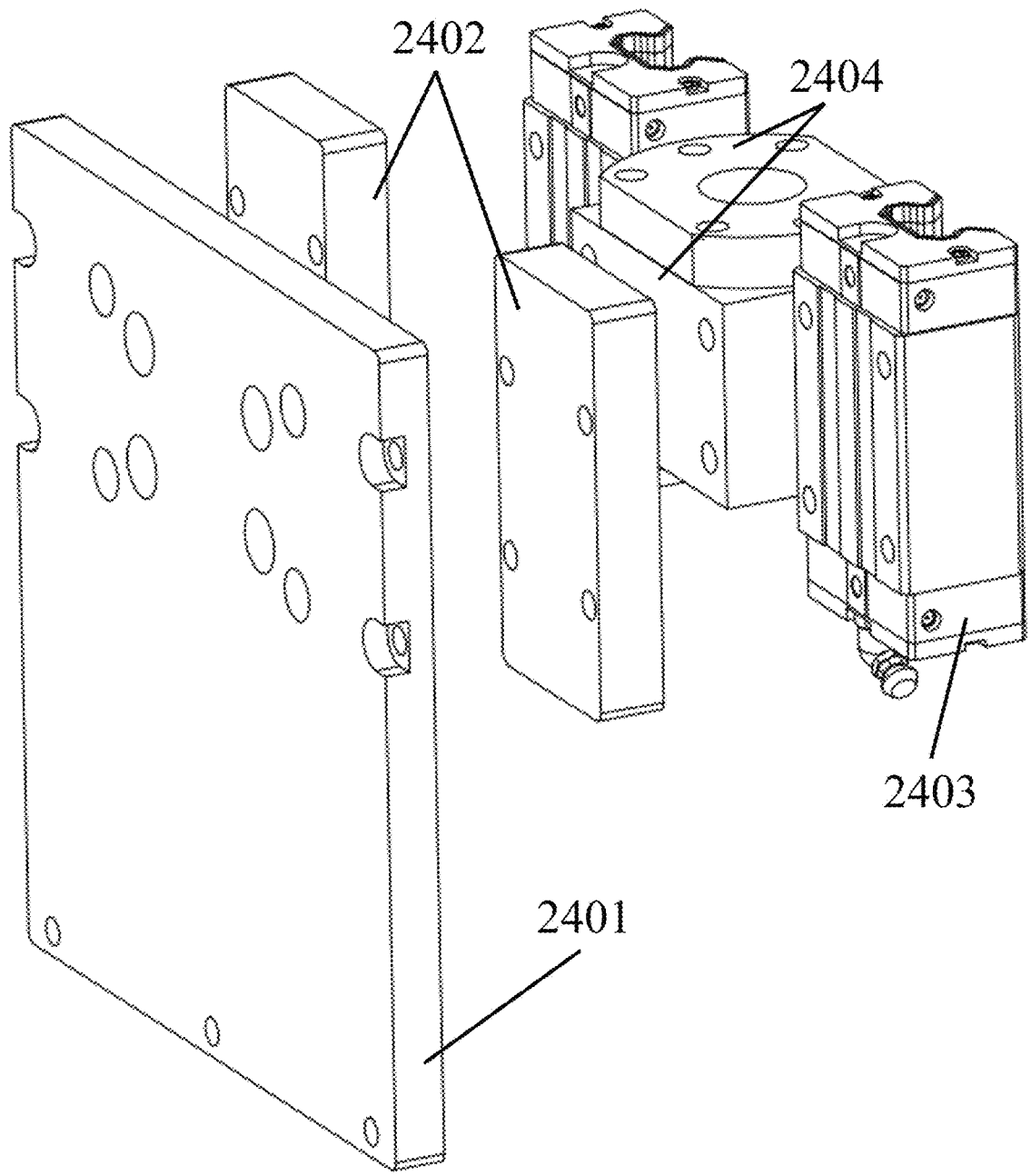
FIG. 21 is a schematic diagram of a flipping fixed structure according to an embodiment of the present invention.

As shown in FIG. 21, the flipping fixed structure 24 comprises a square plate 2401, the square plate 2401 is provided with a padding plate 2402, the padding plate 2402 is provided with a slider III 2403, the slider III 2403 is slidably connected to the guide rail III 2307. The square plate 2401 is provided with a moving seat 2404, and the moving seat 2404 is rotationally sleeved on the screw I 2305. When working, the handwheel 2303 is rotated, which can control the flipping fixed structure 24 along the guide rail III 2307 to do reciprocating motion.

Figure 22:
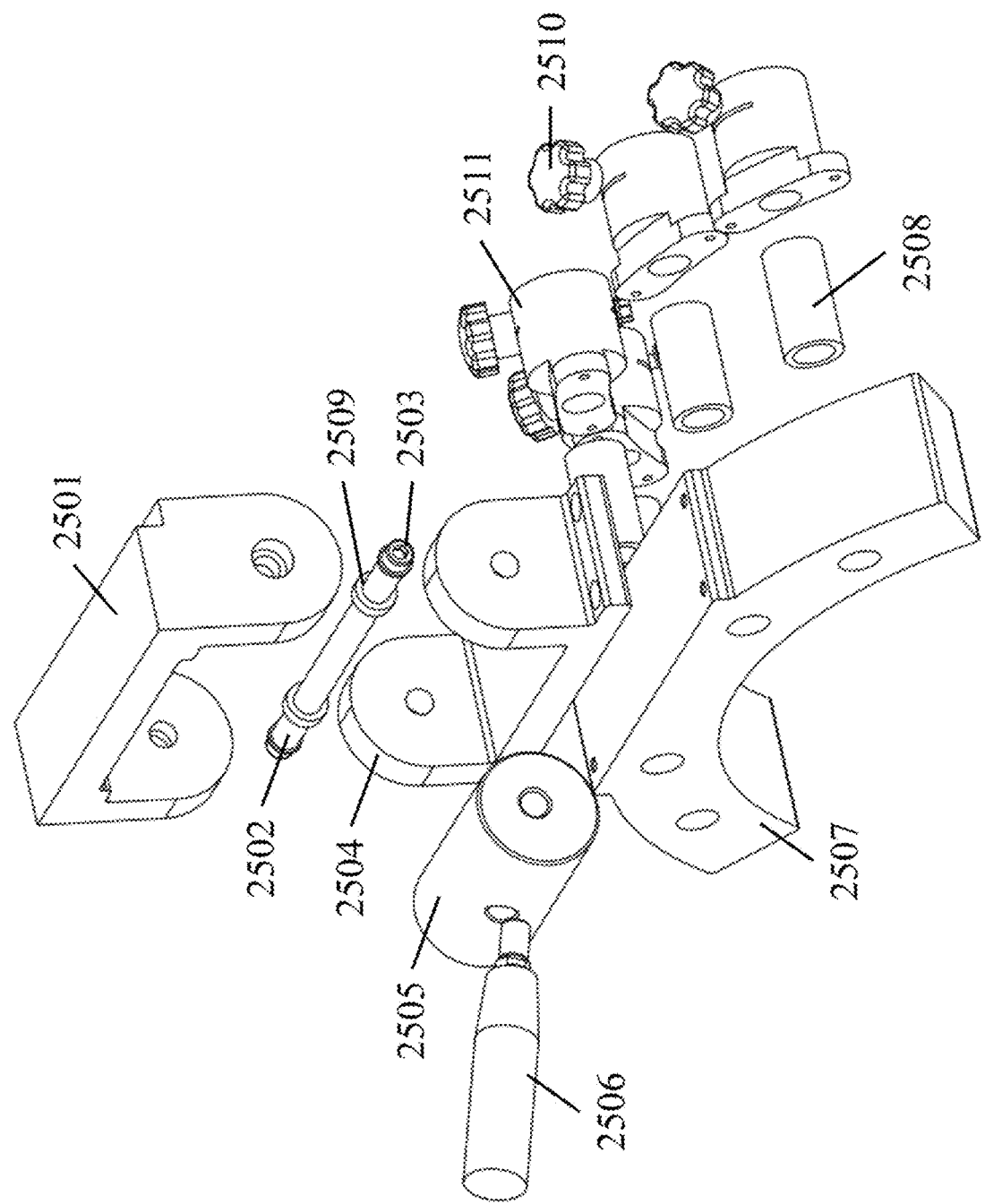
FIG. 22 is a schematic diagram of an auxiliary flipping structure according to an embodiment of the present invention.

As shown in FIG. 22, the auxiliary flipping structure 25 comprises an upper U-shaped ear plate 2501, the upper U-shaped ear plate 2501 connected to the square plate 2401. The upper U-shaped ear plate 2501 is connected to a lower U-shaped ear plate 2504 through a pressing shaft 2502. The pressing shaft 2502 is provided with an eccentric wheel 2505, and the eccentric wheel 2505 is provided with a handle 2506. The two ends of the pressing shaft 2502 are provided with a shaft end screw 2503 for axial limit, the pressing shaft 2502 is provided with two shaft sleeves 2509, and the shaft sleeve 2509 is arranged between the eccentric wheel 2505 and the lower U-shaped ear plate 2504. The bottom end of the lower U-shaped ear plate 2504 is provided with an arc plate 2507, and an auxiliary linear bearing 2508 is arranged in the arc plate 2507. The side of the arc plate 2507 is provided with an auxiliary clamping seat 2511, and the auxiliary clamping seat 2511 is provided with an auxiliary handle 2510. When working, the handle 2506 is held to adjust the eccentric wheel 2505 to a loosening state, so that the upper U-shaped ear plate 2501 and the lower U-shaped ear plate 2504 can rotate relatively, after adjusting to the appropriate position, the eccentric wheel 2505 is adjusted to a pressing state, so that the upper U-shaped ear plate 2501 and the lower U-shaped ear plate 2504 are relatively fixed.

Figure 23:
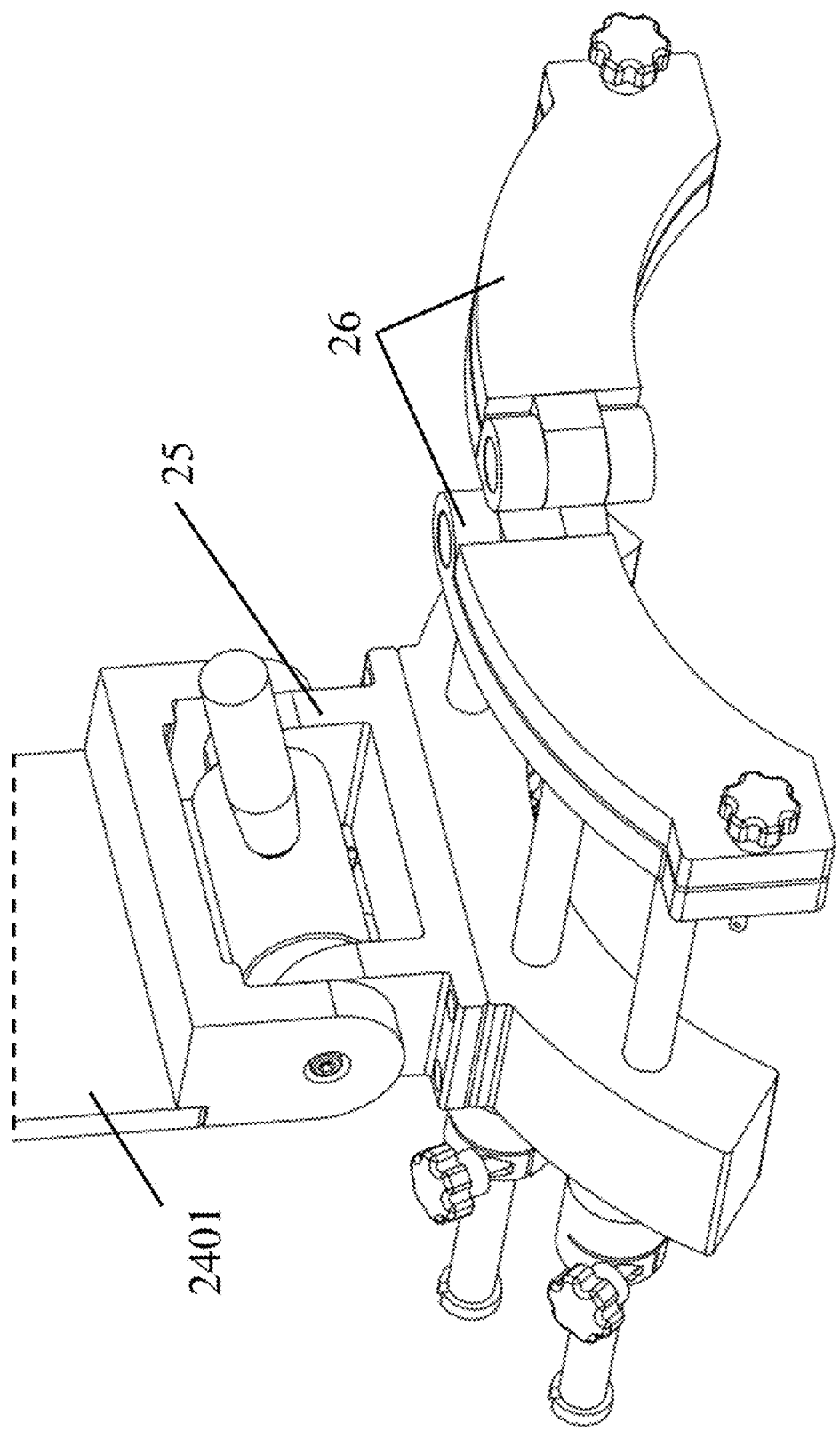
FIG. 23 is a schematic diagram of a connection relationship between a fixed end clamping component and an auxiliary flipping structure according to an embodiment of the present invention.

As shown in FIG. 23, the fixed end clamping component 26 and the mobile end clamping component 17 adopt the same structure, the optical shaft 1711 of the fixed end clamping component 26 is connected to the arc plate 2507 through the auxiliary linear bearing 2508, and the optical shaft 1711 of the fixed end clamping component 26 is clamped in the auxiliary clamping seat 2511. When working, the fixed end clamping component 26 is connected to the auxiliary flipping structure 25, by adjusting the auxiliary clamping seat 2511, the fixed end clamping component 26 and the auxiliary flipping structure 25 can be fixed at any relative position.

Figure 24:
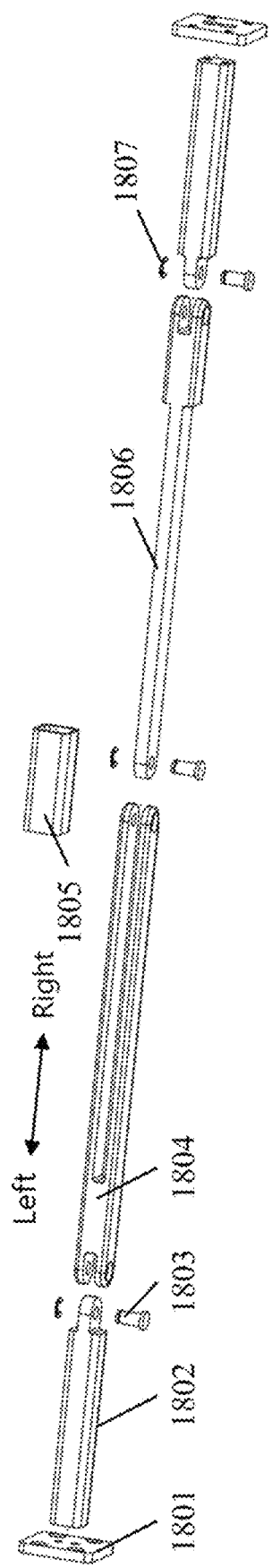
FIG. 24 is a schematic diagram of a connection component according to an embodiment of the present invention.
Figure 25:
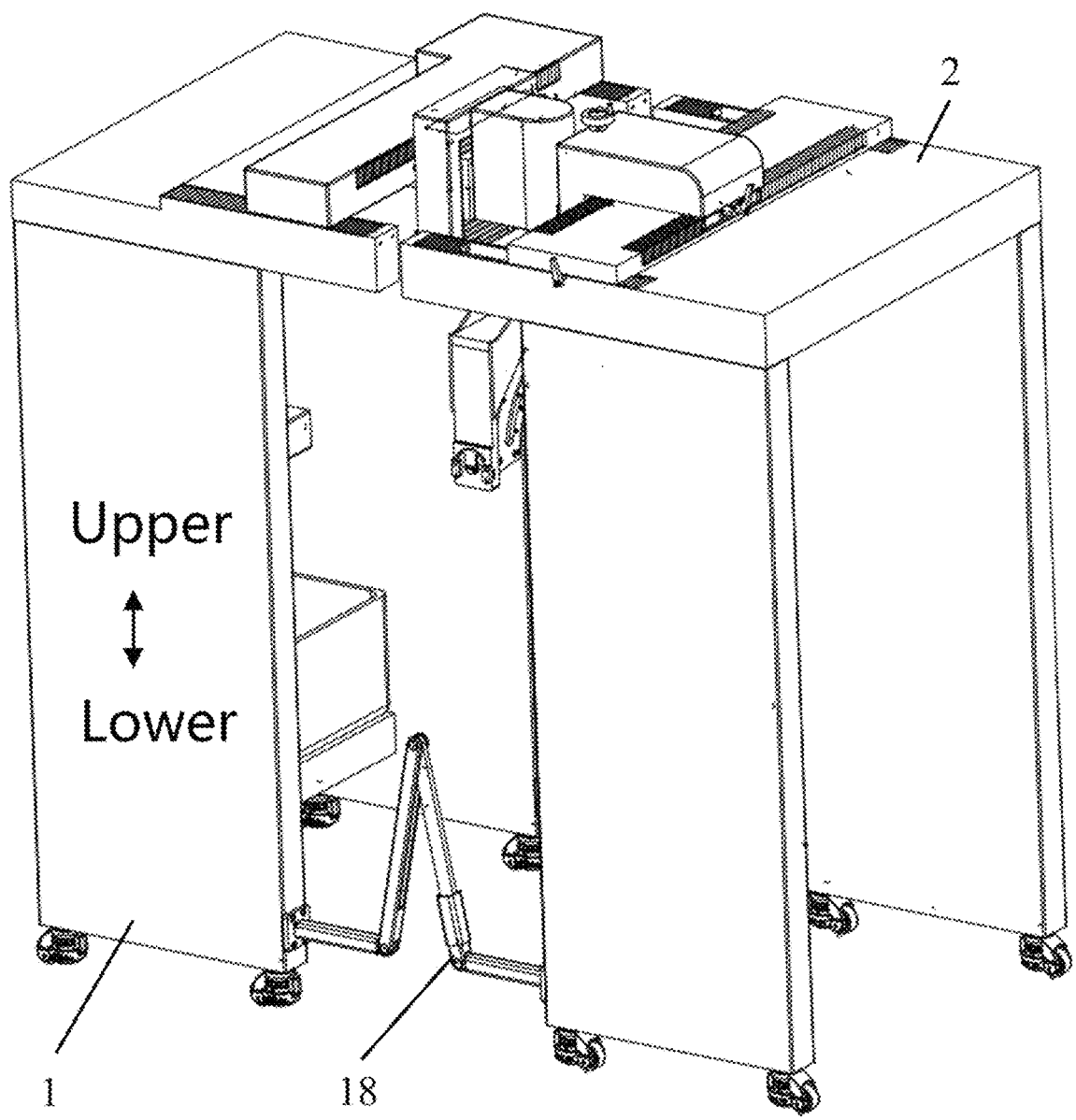
FIG. 25 is a schematic diagram of a contracted state of a robot according to an embodiment of the present invention.

As shown in FIG. 24 and FIG. 25, the connection component 18 comprises two single-ended bent rods 1802, one end of the single-ended bent rod 1802 is connected to the support frame 1101 through a bent rod base plate 1801, the other end of the single-ended bent rod 1802 is rotationally connected to one end of a slotted bent rod 1804 through the rotating shaft 1803. The other end of the slotted bent rod 1804 is rotationally connected to one end of a trimming bent rod 1806 through the rotating shaft 1803. The other end of the trimming bent rod 1806 is rotationally connected to one end of the other single-ended bent rod 1802 through the rotating shaft 1803, and the other end of the single-ended bent rod 1802 is connected to the fixed frame 2101 through the bent rod base plate 1801. A locking sleeve 1805 is slidably arranged on the single-ended bent rod 1802, slotted bent rod 1804 and trimming bent rod 1806. The connection component 18 also comprises a clip spring 1807, the clip spring 1807 is mounted at the end of the rotating shaft 1803 to play an axial limiting role. The locking sleeve 1805 can move left and right along the long axis direction of the slotted bent rod 1804, when the connection component 18 is adjusted to the longest state, the locking sleeve 1805 is moved to the connection between the slotted bent rod 1804 and the trimming bend rod 1806, so as to limit the joint rotation at the connection and realize the fixation of the length of the connection component 18, cooperate with the weight of the mobile end mechanism 1 and the fixed end mechanism 2, the relative fixation of the two positions can be ensured. In the non-working state, in order to reduce the space occupation of the robot and facilitate the storage and placement, to move the locking sleeve 1805 to make it separate from the connection of the rotating shaft 1803, and the connection component 18 is lifted up to rotate the connection of the rotating shaft 1803, meanwhile, the moving end mechanism 1 and the fixed end mechanism 2 are dragged to reduce the relative distance between the two and realize the contraction of the robot.

All the synchronous belt components in the present invention adopt the same existing structure.

Operation process: during the operation, the patient 4 lay flat on the operating bed 3, when the doctor completed the Kirschner wire insertion, the robot is pushed to move along the length of the operating bed 3, so that the self-rotating component 16 is approximately located above the wound of patient 4; after reaching the specified position, the locking sleeve 1805 is adjusted to make the mobile end mechanism 1 and the fixed end mechanism 2 move relatively far away from the motion, after moving to the connection component 18 to the maximum length, the locking sleeve 1805 is adjusted to the locking position to ensure the relative fixation of the mobile end mechanism 1 and the fixed end mechanism 2; the mobile end clamping component 17 and the fixed end clamping component 26 are taken out from the storage box 1110 and connected to the mobile end mechanism 1 and the fixed end mechanism 2 respectively; The host computer sends signals to control the motion of each joint of the mobile end mechanism 1, and at the same time adjusts the relative position of the mobile end clamping component 17 and the self-rotating component 16 until it can clamp the Kirschner wire at the distal end of the patient 4 fracture, and then adjusts the traction gripper 2205, handwheel 2303, translation gripper 2311 and eccentric wheel 2505 to the loose state, holding the arc plate 2507 to drag its motion, and adjusting the relative position of the fixed end clamping component 26 and the auxiliary flipping structure 25, until it can hold the proximal Kirschner wire of patient 4 fracture, after clamping, the traction gripper 2205, handwheel 2303, translation gripper 2311 and eccentric wheel 2505 are adjusted again to make it locked, so that the structure of each component of the fixed end mechanism 2 except the fixed end clamping component 26 is relatively fixed; after clamping, the kirschner wire can be fixed on the mobile end clamping component 17 and the fixed end clamping component 26 by adjusting the rotating handle 1709 and the butterfly nut 1710, the clamping seat 1619 is adjusted to realize the fixed connection between the mobile end clamping component 17 and the self-rotating component 16, the auxiliary clamping seat 2511 is adjusted to realize the fixed connection between the fixed end clamping component 26 and the auxiliary flipping structure 25; the above steps enable the robot to connect with patient 4.

After the above steps are completed, the six-degree-of-freedom motion of the space required for fracture reduction based on the preoperative patient's 4 CT or X-ray image is input into the host computer of the robot, the host computer sends a signal to control the motion of each joint of the mobile end mechanism 1, so as to drive the distal motion of the patient's 4 fracture to align it with the proximal end of the fracture and finally achieve the reduction operation. After the reduction, the doctor carries out the fixed operation, after the operation is completed, the kirschner wire is separated from the mobile end clamping component 17 and the fixed end clamping component 26 by adjusting the rotating handle 1709 and the butterfly nut 1710, the mobile end clamping component 17 and the self-rotating component 16 are separated by adjusting the clamping seat 1619, the fixed end clamping component 26 and the auxiliary flipping component 15 are separated by adjusting the auxiliary clamping seat 2511, the mobile end clamping component 17 and the fixed end clamping component 26 are removed and put back into the storage box 1110; the traction gripper 2205, handwheel 2303, auxiliary gripper and eccentric wheel 2505 are adjusted to the loose state, and the arc plate 2507 is grasped to drag it to move, so that each part of the fixed end mechanism 2 is restored to the initial position, at the same time, the host computer sends a signal to control the motion of each joint of the mobile end mechanism 1, so that each part of the mobile end mechanism 1 is restored to the initial position, the mobile end mechanism 1 and the fixed end mechanism 2 can move relatively close to each other by adjusting the locking sleeve 1805, after moving to the initial state of the robot, the robot is pushed away from patient 4 along the length direction of the operating bed 3, and the robot is moved to the preoperative position.

A frame-type surgical robot for fracture reduction of the present invention has a wide motion range of six-degree-of-freedom, and the joint motion stroke to achieve reduction is: the traction stroke is not less than 100 mm, the translation stroke is not less than 50 mm, the lifting stroke is not less than 50 mm, the angle displacement correction angle is not less than 30°, and the self-rotating correction angle around the bone axis is not less than +45°, which is suitable for different reduction stroke requirements such as embedded fractures.

Therefore, the present invention adopts a frame-type surgical robot for fracture reduction, which not only has a high load, a compact structure, a small footprint, and a wide range of motion but also combines manual and electric adjustment, which is a simple operation and a strong applicability.

Finally, it should be noted that the above examples are merely used for describing the technical solutions of the present invention, rather than limiting the same. Although the present invention has been described in detail with reference to the preferred examples, those of ordinary skill in the art should understand that the technical solutions of the present invention may still be modified or equivalently replaced. However, these modifications or substitutions should not make the modified technical solutions deviate from the spirit and scope of the technical solutions of the present invention.

What is claimed is:

1. A frame-type surgical robot for fracture reduction, comprising a mobile end mechanism and a fixed end mechanism, the mobile end mechanism is connected to the fixed end mechanism through a connection component, the mobile end mechanism comprises a traction component, the traction component is connected to a lifting component through a translation component, the lifting component is connected to a flipping component through a swing component, the flipping component is provided with a self-rotating component, and the self-rotating component is provided with a mobile end clamping component; the fixed end mechanism comprises an auxiliary traction structure, the auxiliary traction structure is connected to a hand-cranking lifting structure through an auxiliary translation structure, the hand-cranking lifting structure is connected to an auxiliary flipping structure through a flipping fixed structure, the auxiliary flipping structure is provided with a fixed end clamping component, during the operation, a surgical robot is placed above the operating bed to complete the fracture reduction operation of the patient;

the flipping component comprises a support frame, one end of the support frame is provided with a left lug with a left groove and an installation groove, the other end of the support frame is provided with a right lug with a right groove, the left groove and the right groove are respectively provided with a flipping bearing;

the self-rotating component comprises a gearbox, the two ends of the gearbox are respectively provides with a left shaft and a right shaft, the gearbox is connected to the flipping bearing of the left groove of the support frame through the left shaft, the left shaft is provided with a left shaft snap ring and a flipping baffle for the flipping limit, the gearbox is connected to the flipping bearing of the right groove of the support frame through the right shaft, the right shaft is provided with a right shaft snap ring, and the right shaft passes through the right groove of the support frame and is rotationally connected to a flipping synchronous belt component; the gearbox is provided with a front cover plate, the gearbox is provided with a gear, the outer surface of the gearbox is provided with a joint motor, the output shaft of the joint motor is connected to the gear, the gear is meshed with a ring gear, and the ring gear is slidably connected to the gearbox through a roller, a rear insert strip is arranged between one side of the ring gear and the gearbox, a front insert strip is arranged between the other side of the ring gear and the front cover plate, and the ring gear is provided with linear bearings; the gearbox is provided with a clamping seat, and the clamping seat is provided with a locking handle;

the mobile end clamping component comprises four optical shafts, the optical shafts are connected to the ring gear through the linear bearing, and the optical shaft is clamped in the clamping seat; one end of the four optical shafts is provided with a carbon ring, wherein the other end of the two optical shafts is connected to a left inner splint, the other end of the other two optical shafts is connected to a right inner splint, one end of the left inner splint is connected to a left outer splint through a rotating shaft, the other end of the left inner splint is connected to the left outer splint through a rotating handle, one end of the right inner splint is connected to a right outer splint through the rotating shaft, the other end of the right inner splint is connected to the right outer splint through the rotating handle, a Kirschner wire is clamped between the left inner splint and the left outer splint, and between the right inner splint and the right outer splint.

2. The frame-type surgical robot for fracture reduction according to claim 1, the traction component comprises a support frame, the side and top end of the support frame are provided with a support frame sheet metal, the bottom end of the support frame is connected to a caster through a hole flat connector, the support frame is provided with a motor support plate, the motor support plate is provided with a traction push rod, the two sides of the traction push rod are provided with a traction guide rail, the traction guide rail is arranged on the support frame, the traction push rod is connected to a push rod mounting frame through a push rod bracket, the push rod mounting frame is fixed on the support frame, and the support frame sheet metal at the top is provided with a traction organ cover for protection; the support frame is provided with a cross-bed connecting rod and a counterweight block, the counterweight block is provided with a storage box, the storage box is connected to the counterweight block through a bulge.

3. The frame-type surgical robot for fracture reduction according to claim 2, the translation component comprises a translation bottom plate, the bottom of the translation bottom plate is provided with a module connector, a movable rod of the traction push rod is connected to the module connector, the bottom of the translation bottom plate is provided with a traction slider, and the traction slider is slidably connected to the traction guide rail; the top of the translation bottom plate is covered with a translation sheet metal, and the translation sheet metal is provided with a translation organ cover for protection, the two ends of the translation bottom plate are respectively provided with a translation side plate and a translation motor plate, a translation screw is arranged between the translation side plate and the translation motor plate, both sides of the translation screw is provided with a translation guide rail, the translation guide rail is arranged on the translation bottom plate, the two ends of the translation screw are respectively connected to the translation side plate and the translation motor plate through a translation bearing, the translation motor plate is provided with a translation motor, the output shaft of the translation motor is in transmission connection with one end of the translation screw through a translation synchronous belt component, one side of the translation motor plate is fixed with a tensioning bulge for the tensioning of the translation synchronous belt component, the tensioning bulge is connected to a translation tensioning plate through a single bolt, and the translation bottom plate is provided with a translation limit part for translation limit.

4. The frame-type surgical robot for fracture reduction according to claim 3, the lifting component comprises a lifting bottom plate, the lifting bottom plate is connected to a translation slide through a slide side plate, the bottom end of the translation slide is provided with a connecting seat and a translation slider, the translation slider is slidably connected to the translation guide rail, the translation slider is arranged on both sides of the connecting seat, the connecting seat is provided with a screw nut, the screw nut is sleeved on the translation screw and rotationally connected to the translation screw, and the translation slide is provided with a translation baffle for the translation limit; the upper of the lifting bottom plate is covered with a lifting sheet metal, the lifting sheet metal is provided with a lifting organ cover for protection, both ends of the lifting bottom plate is provided with a lifting side plate and a lifting motor plate, a lifting screw is arranged between the lifting side plate and the lifting motor plate, both sides of the lifting screw is provided with a lifting guide rail, the lifting guide rail is arranged on the lifting bottom plate, the two ends of the lifting screw are respectively connected to the lifting side plate and the lifting motor plate through a lifting bearing, the lifting motor plate is provided with a lifting motor, the output shaft of the lifting motor is in transmission connection with one end of the lifting screw through a lifting synchronous belt component, one side of the lifting motor plate is fixed with a lifting bulge for the tensioning of the lifting synchronous belt component, the lifting bulge is connected to a lifting tensioning plate through a single bolt, and the lifting bottom plate is provided with a lifting limit part for lifting limit.

5. The frame-type surgical robot for fracture reduction according to claim 4, the swing component comprises a sensor fixed plate, the sensor fixed plate is connected to a lifting seat through a lifting slide, the lifting seat is provided with a lifting nut, the lifting nut is sleeved on the lifting screw and is rotationally connected to the lifting screw, the two sides of the lifting seat are provided with a lifting slider, one side of the lifting slider is connected to a lifting slide, the other side of the lifting slider is slidably connected to the lifting guide rail, and the lifting slide is provided with a lifting baffle for the lifting limit; the sensor fixed plate is provided with a sensor, and the sensor is connected to a sensor adapter plate, the sensor adapter plate is provided with a swing reducer, and the swing reducer is connected to the output shaft of a swing motor; the lifting slide is connected to a swing sheet metal, and the swing sheet metal is covered on the sensor fixed plate, sensor, sensor adapter plate, swing reducer and swing motor.

6. The frame-type surgical robot for fracture reduction according to claim 5, the support frame is provided with an array hole, and the swing reducer is in transmission connection with the support frame through an array hole; the left lug is provided with a flipping limit part for limiting the flipping limit, the support frame is provided with a step surface, the step surface is provided with a flipping reducer, the flipping reducer is connected to the output shaft of a flipping motor, the flipping reducer is in transmission connection with a flipping synchronous belt component, a flipping motor plate is arranged between the flipping reducer and the flipping synchronous belt component, the flipping motor plate is provided with a straight groove for adjusting the tension of the flipping synchronous belt component, the straight groove is provided with an installation hole, the installation hole is arranged on the support frame, and the upper of the support frame is covered with a flipping sheet metal.

7. The frame-type surgical robot for fracture reduction according to claim 6, the auxiliary traction structure comprises a fixed frame, both sides and the top of the fixed frame are provided with a shell, the bottom of the fixed frame is connected to an auxiliary caster through a connecting plate, the top of the fixed frame is provided with a fixed plate, the fixed plate is provided with a guide rail I, the guide rail I is arranged in the shell at the top of the fixed frame, and the shell at the top of the fixed frame is provided with an organ cover I for protection;

the auxiliary translation structure comprises a bottom plate I, the bottom end of the bottom plate I is provided with a slider I, and the slider I is slidably connected to the guide rail I, the bottom end of the bottom plate I is connected to a traction gripper through a cushion block I, the upper of the bottom plate I is covered with a rectangular shell, and the rectangular shell is provided with an organ cover II, the top of the bottom plate I is provided with a guide rail II;

the hand-cranking lifting structure comprises a bottom plate II, one side of the bottom plate II is provided with an L-shaped plate, the bottom end of the L-shaped plate is provided with a slider II, the slider II is slidably connected to the guide rail II, the bottom end of the L-shaped plate is connected to a translation gripper through a cushion block II, both ends of the bottom plate II are provided with a vertical plate, the other side of the bottom plate II is provided with a guide rail II and a screw I, both ends of the screw I are connected to the vertical plate through an auxiliary bearing, one end of the screw I is provided with a handwheel, the bottom plate II is connected to an L-shaped shell, the L-shaped shell is covered on the screw I, the guide rail II and the L-shaped plate, and the L-shaped shell is provided with an organ cover II;

the flipping fixed structure comprises a square plate, the square plate is provided with a padding plate, the padding plate is provided with a slider III, the slider II is slidably connected to the guide rail I, the square plate is provided with a moving seat, and the moving seat is rotationally sleeved on the screw I;

the auxiliary flipping structure comprises an upper U-shaped ear plate, the upper U-shaped ear plate connected to the square plate, the upper U-shaped ear plate connected to a lower U-shaped ear plate through a pressing shaft, the pressing shaft is provided with an eccentric wheel, the eccentric wheel is provided with a handle, the bottom end of the lower U-shaped ear plate is provided with an arc plate, an auxiliary linear bearing is arranged in the arc plate, the side of the arc plate is provided with an auxiliary clamping seat, and the auxiliary clamping seat is provided with an auxiliary handle;

the fixed end clamping component and the mobile end clamping component adopt the same structure, the optical shaft of the fixed end clamping component is connected to the arc plate through the auxiliary linear bearing, and the optical shaft of the fixed end clamping component is clamped in the auxiliary clamping seat.

8. The frame-type surgical robot for fracture reduction according to claim 7, the connection component comprises two single-ended bent rods, one end of the single-ended bent rod is connected to the support frame through a bent rod base plate, and the other end of the single-ended bent rod is rotationally connected to one end of a slotted bent rod through the rotating shaft, the other end of the slotted bent rod is rotationally connected to one end of a trimming bent rod through the rotating shaft, the other end of the trimming bent rod is rotationally connected to one end of the other single-ended bent rod through the rotating shaft, and the other end of the other single-ended bent rod is connected to the fixed frame through the bent rod base plate, a locking sleeve is slidably arranged on the single-ended bent rod, slotted bent rod and trimming bent rod.

* * * * *